(12) United States Patent
Liu et al.

(10) Patent No.: US 8,865,875 B2
(45) Date of Patent: Oct. 21, 2014

(54) SITE-SPECIFIC ATTACHMENT OF DRUGS OR OTHER AGENTS TO ENGINEERED ANTIBODIES WITH C-TERMINAL EXTENSIONS

(75) Inventors: Jie Liu, Palo Alto, CA (US); David King, Solana Beach, CA (US)

(73) Assignee: Medarex, L.L.C., Princeton, NJ (US)

( * ) Notice: Subject to any disclaimer, the term of this patent is extended or adjusted under 35 U.S.C. 154(b) by 1214 days.

(21) Appl. No.: 12/674,503

(22) PCT Filed: Aug. 19, 2008

(86) PCT No.: PCT/US2008/073569
§ 371 (c)(1),
(2), (4) Date: Aug. 4, 2011

(87) PCT Pub. No.: WO2009/026274
PCT Pub. Date: Feb. 26, 2009

(65) Prior Publication Data
US 2011/0280891 A1    Nov. 17, 2011

Related U.S. Application Data

(60) Provisional application No. 60/957,271, filed on Aug. 22, 2007.

(51) Int. Cl.
| | |
|---|---|
| C07K 16/00 | (2006.01) |
| C07K 16/46 | (2006.01) |
| A61K 47/48 | (2006.01) |
| C07K 16/28 | (2006.01) |
| C07K 16/30 | (2006.01) |

(52) U.S. Cl.
CPC ....... *C07K 16/2875* (2013.01); *A61K 47/48638* (2013.01); *A61K 47/48446* (2013.01); *A61K 47/48392* (2013.01); *A61K 47/48715* (2013.01); *C07K 2317/21* (2013.01); *A61K 47/48384* (2013.01); *C07K 16/3069* (2013.01)
USPC .................. 530/391.5; 530/387.1; 530/387.3; 530/387.7; 530/388.2; 530/391.3; 530/391.7

(58) Field of Classification Search
USPC .......... 530/387.1, 387.3, 387.7, 388.2, 391.3, 530/391.5, 391.7
See application file for complete search history.

(56) References Cited

U.S. PATENT DOCUMENTS

| | | | |
|---|---|---|---|
| 4,391,904 A | 7/1983 | Litman et al. | |
| 4,698,420 A | 10/1987 | Urnovitz | |
| 4,912,227 A | 3/1990 | Kelly et al. | |
| 4,978,757 A | 12/1990 | Kelly et al. | |
| 5,070,092 A | 12/1991 | Kanda et al. | |
| 5,084,468 A | 1/1992 | Saito et al. | |
| 5,101,038 A | 3/1992 | Nakano et al. | |
| 5,187,186 A | 2/1993 | Kanda et al. | |
| 5,219,996 A | 6/1993 | Bodmer et al. | |
| 5,332,837 A | 7/1994 | Kelly et al. | |
| 5,641,780 A | 6/1997 | Amishiro et al. | |
| 5,703,080 A | 12/1997 | Nakakura et al. | |
| 5,739,350 A | 4/1998 | Kelly et al. | |
| 6,214,345 B1 | 4/2001 | Firestone et al. | |
| 6,989,452 B2 | 1/2006 | Ng et al. | |
| 7,012,135 B2 | 3/2006 | Athwal et al. | |
| 7,087,600 B2 | 8/2006 | Ng et al. | |
| 7,090,843 B1 | 8/2006 | Francisco et al. | |
| 7,091,186 B2 | 8/2006 | Senter et al. | |
| 7,129,261 B2 | 10/2006 | Ng et al. | |
| 7,311,902 B2 | 12/2007 | Bam et al. | |
| 7,335,748 B2 | 2/2008 | Harkins et al. | |
| 7,342,110 B2 | 3/2008 | Hoffee et al. | |
| 7,387,776 B2 | 6/2008 | Keler et al. | |
| 7,517,903 B2 | 4/2009 | Chen et al. | |
| 7,521,541 B2 | 4/2009 | Eigenbrot et al. | |
| 7,553,816 B2 | 6/2009 | Senter et al. | |
| 7,691,962 B2 | 4/2010 | Boyd et al. | |
| 7,714,016 B2 | 5/2010 | Gangwar et al. | |
| 2003/0161809 A1 | 8/2003 | Houston et al. | |
| 2005/0180972 A1 | 8/2005 | Wahl et al. | |
| 2005/0201994 A1 | 9/2005 | Korman et al. | |
| 2005/0266008 A1 | 12/2005 | Graziano et al. | |
| 2007/0160817 A1 | 7/2007 | Roh | |
| 2010/0145036 A1* | 6/2010 | Sufi et al. ...................... | 536/17.4 |

FOREIGN PATENT DOCUMENTS

| | | |
|---|---|---|
| EP | 0 088 695 | 9/1983 |
| EP | 0 537 575 | 4/1993 |
| WO | WO 81/01145 | 4/1981 |
| WO | WO 96/10405 | 4/1996 |
| WO | WO 02/083180 | 10/2002 |
| WO | WO 02/096910 | 12/2002 |
| WO | WO 2004/073656 | 9/2004 |
| WO | WO 2005/112919 | 12/2005 |
| WO | WO 2007/002223 | 1/2007 |
| WO | WO 2007/038637 | 4/2007 |
| WO | WO 2007/038658 | 4/2007 |
| WO | WO 2007/051081 | 5/2007 |
| WO | WO 2007/059404 | 5/2007 |
| WO | WO 2007/067730 | 6/2007 |
| WO | WO 2007/067991 | 6/2007 |

(Continued)

OTHER PUBLICATIONS

George et al. (Proc. Natl. Acad. Sci. USA. Aug. 29, 1995; 92 (18): 8358-62).*

(Continued)

*Primary Examiner* — Stephen Rawlings
(74) *Attorney, Agent, or Firm* — Yuan Chao

(57) ABSTRACT

The present invention provides antibodies (e.g., IgG antibodies) having C-terminal cysteine-containing extensions that facilitate antibody conjugation to a partner molecule (e.g. a drug, toxin, marker molecule, protein, radioisotope, or other therapeutic agent). Methods of making, screening and selecting the antibodies of the invention are provided.

11 Claims, 8 Drawing Sheets

(56) References Cited

FOREIGN PATENT DOCUMENTS

| WO | WO 2007/089100 | 8/2007 |
| --- | --- | --- |
| WO | WO 2008/074004 | 6/2008 |
| WO | WO 2008/083312 | 7/2008 |
| WO | WO 2008/103693 | 8/2008 |
| WO | WO 2008/141044 | 11/2008 |
| WO | WO 2009/045957 | 4/2009 |
| WO | WO 2009/052249 | 4/2009 |

OTHER PUBLICATIONS

McCartney et al. (Protein Eng. Mar. 1995; 8 (3): 301-14).*
Cumber et al. (J. Immunol. Jul. 1, 1992; 149 (1): 120-6).*
Dorai et al. (Biotechnology (NY). Sep. 1994; 12 (9): 890-7).*
Kipriyanov et al. (Mol. Immunol. Oct. 1994; 31 (14): 1047-58).*
Allen, T.M., "Ligand-Targeted Therapeutics in Anticancer Therapy", Nature Reviews Cancer, vol. 2, pp. 750-763 (2002).
Beeram, M. et al., "A phase I study of trastuzumab-DM1 (T-DMI), a first-in-class HER2 antibody-drug conjugate (ADC), in patients (pts) with advanced HER2+ breast cancer (BC)", J. Clin. Oncol., Abstract No. 1087, vol. 26, No. 15S, p. 48s (2008).
Boger, D.L. et al., "CC-1065 and the Duocarmycins: Synthetic Studies", Chemical Reviews, vol. 97, No. 3, pp. 787-828 (1997).
Boger, D.L. et al., "CC-1065 and the Duocarmycins: Understanding their Biological Function through Mechanistic Studies", Angew. Chem. Int. Ed. Engl., vol. 35, pp. 1438-1474 (1996).
Bouvier, J. et al., "Leishmanolysin: Surface Metalloproteinase of *Leishmania*", Methods in Enzymology, vol. 248, pp. 614-633 (1995).
Carl, P.L. et al., "A Novel Connector Linkage Applicable in Prodrug Design", Journal of Medicinal Chemistry, vol. 24, No. 5, pp. 479-480 (1981).
Caron, P.C. et al., "Engineered Humanized Dimeric Forms of IgG are More Effective Antibodies", J. Exp. Med., vol. 176, pp. 1191-1195 (1992).
Chilkoti, A. et al., "Site-Specific Conjugation of a Temperature-Sensitive Polymer to a Genetically-Engineered Protein", Bioconjugate Chem., vol. 5, No. 6, pp. 504-507 (1994).
Cumber, A.J. et al., "Comparative Stabilities In Vitro and In Vivo of a Recombinant Mouse Antibody FvCys Fragment and a bisFvCys Conjugate", The Journal of Immunology, vol. 149, No. 1, pp. 120-126 (1992).
de Groot, F.M.H. et al., "Elongated Multiple Electronic Cascade and Cyclization Spacer Systems in Activatible Anticancer Prodrugs for Enhanced Drug Release", J. Org. Chem., vol. 66, No. 26, pp. 8815-8830 (2001).
de Groot, F.M.H. et al., "Synthesis and Biological Evaluation of Novel Prodrugs of Anthracyclines for Selective Activation by the Tumor-Associated Protease Plasmin", Journal of Medicinal Chemistry, vol. 42, No. 25, pp. 5277-5283 (1999).
de Groot, F.M.H. et al., "Synthesis and Biological Evaluation of 2'-Carbamate-Linked and 2'-Carbonate-Linked Prodrugs of Paclitaxel: Selective Activation by the Tumor-Associated Protease Plasmin", Journal of Medicinal Chemistry, vol. 43, No. 16, pp. 3093-3102 (2000).
Doronina, S.O. et al., "Development of potent monoclonal antibody auristatin conjugates for cancer therapy", Nature Biotechnology, vol. 21, No. 7, pp. 778-784 (2003).
Dubowchik, G.M. et al., "Cathepsin B-Sensitive Dipeptide Prodrugs. 2. Models of Anticancer Drugs Paclitaxel (Taxol®), Mitomycin C and Doxorubicin", Bioorganic & Medicinal Chemistry Letters, vol. 8, pp. 3347-3352 (1998).
Dunn, B.M. et al., "Subsite Preferences of Retroviral Proteinases", Methods in Enzymology, vol. 241, pp. 254-278 (1994).
Fisch, I. et al., "Site-Specific Modification of a Fragment of a Chimeric Monoclonal Antibody Using Reverse Proteolysis", Bioconjugate Chem., vol. 3, No. 2, pp. 147-153 (1992).
Garnett, M.C., "Targeted drug conjugates: principles and progress", Advanced Drug Delivery Reviews, vol. 53, pp. 171-176 (2001).

Greenwood, J. et al., "Engineering multiple-domain forms of the therapeutic antibody CAMPATH-1H: effects on complement lysis", Therapeutic Immunology, vol. 1, pp. 247-255 (1994).
Hardy, J. et al., "Genetic Variability and Alzheimer's Disease", Amyloid Protein Precursor in Development, Aging and Alzheimer's Disease, pp. 190-198, Springer-Verlag, publ., Masters, C.L., et al., eds. (1994).
Hemminki, A. et al., "Introduction of lysine residues on the light chain constant domain improves the labelling properties of a recombinant Fab fragment", Protein Engineering, vol. 8, No. 2, pp. 185-191 (1995).
King, D.J. et al., "Improved Tumor Targeting with Chemically Cross-Linked Recombinant Antibody Fragments", Cancer Research, vol. 54, pp. 6176-6185 (1994).
Kovtun, Y.V. et al., "Antibody-Drug Conjugates Designed to Eradicate Tumors with Homogeneous and Heterogeneous Expression of the Target Antigen", Cancer Res., vol. 66, No. 6, pp. 3214-3221 (2006).
Kuan, C.-T. et al., "*Pseudomonas* Exotoxin a Mutants. Replacement of Surface Exposed Residues in Domain II with Cysteine Residues that Can Be Modified with Polyethylene Glycol in a Site-Specific Manner", The Journal of Biological Chemistry, vol. 269, No. 10, pp. 7610-7616 (1994).
Leung, S. et al., "Engineering a Unique Glycosylation Site for Site-Specific Conjugation of Haptens to Antibody Fragments", The Journal of Immunology, vol. 154, pp. 5919-5926 (1995).
Li, L. et al., "Reduction of Kidney Uptake in Radiometal Labeled Peptide Linkers Conjugated to Recombinant Antibody Fragments. Site-Specific Conjugation of DOTA-Peptides to a Cys-Diabody", Bioconjugate Chem., vol. 13, No. 5, pp. 985-995 (2002).
Lyons, A. et al., "Site-specific attachment to recombinant antibodies via introduced surface cysteine residues", Protein Engineering, vol. 3, No. 8, pp. 703-708 (1990).
Matayoshi, E.D. et al., "Novel Fluorogenic Substrates for Assaying Retroviral Proteases by Resonance Energy Transfer", Science, vol. 247, pp. 954-958 (1990).
Olafsen, T. et al., "Covalent disulfide-linked anti-CEA diabody allows site-specific conjugation and radiolabeling for tumor targeting applications", Protein Engineering, Design & Selection, vol. 17, No. 1, pp. 21-27 (2004).
Packard, B. et al., "Site-Directed Labeling of a Monoclonal Antibody: Targeting to a Disulfide Bond", Biochemistry, vol. 25, No. 12, pp. 3458-3552 (1986).
Pastan, I. et al., "Immunotoxins in cancer therapy", Current Opinion in Investigational Drugs, vol. 3, No. 7, pp. 1089-1091 (2002).
Payne, G., "Progress in immunoconjugate cancer therapeutics", Cancer Cell, vol. 3, pp. 207-212 (2003).
Rodwell, J.D. et al., "Site-specific covalent modification of monoclonal antibodies: In vitro and in vivo evaluations", Proc. Natl. Acad. Sci. USA, vol. 83, pp. 2632-2636 (1986).
Saito, G. et al., "Drug delivery strategy utilizing conjugation via reversible disulfide linkages: role and site of cellular reducing activities", Advanced Drug Delivery Reviews, vol. 55, pp. 199-215 (2003).
Seidah, N.G. et al., "Pro-Protein Convertases of Subtilisin/Kexin Family", Methods in Enzymology, vol. 244, pp. 175-188 (1994).
Senter, P.D. et al., "Selective activation of anticancer prodrugs by monoclonal antibody-enzyme conjugates", Advanced Drug Delivery Reviews, vol. 53, pp. 247-264 (2001).
Smith, M.C. et al., "Purification and Kinetic Characterization of Human Cytomegalovirus Assemblin", Methods in Enzymology, vol. 244, pp. 412-423 (1994).
Stimmel, J.B. et al., "Site-specific Conjugation on Serine → Cysteine Variant Monoclonal Antibodies", The Journal of Biological Chemistry, vol. 275, No. 39, pp. 30445-30450 (2000).
Thornberry, N.A. et al., "Interleukin-1β Converting Enzyme", Methods in Enzymology, vol. 244, pp. 615-631 (1994).
Toki, B.E. et al., "Protease-Mediated Fragmentation of *p*-Amidobenzyl Ethers: a New Strategy for the Activation of Anticancer Prodrugs", J. Org. Chem., vol. 67, No. 6, pp. 1866-1872 (2002).
Trail, P.A. et al., "Monoclonal antibody drug immunoconjugates for targeted treatment of cancer", Cancer Immunol. Immunother., vol. 52, pp. 328-337 (2003).

(56) References Cited

OTHER PUBLICATIONS

Weber, J.M. et al., "Adenovirus Endopeptidases", Methods in Enzymology, vol. 244, pp. 595-604 (1994).

Yang, K. et al., "Tailoring structure-function and pharmacokinetic properties of single-chain Fv proteins by site-specific PEGylation", Protein Engineering, vol. 16, No. 10, pp. 761-770 (2003).

Albrecht, H. et al., "Production of Soluble ScFvs with C-Terminal-Free Thiol for Site-Specific Conjugation or Stable Dimeric ScFvs on Demand", Bioconjugate Chem., vol. 15, No. 1, pp. 16-26 (2004).

Hamblett, K.J. et al., "Effects of Drug Loading on the Antitumor Activity of a Monoclonal Antibody Drug Conjugate", Clinical Cancer Research, vol. 10, pp. 7063-7070 (2004).

Henry, M.D. et al., "A Prostate-Specific Membrane Antigen-Targeted Monoclonal Antibody-Chemotherapeutic Conjugate Designed for the Treatment of Prostate Cancer", Cancer Research, vol. 64, pp. 7995-8001 (2004).

Junutula, J.R. et al., "Site-specific conjugation of a cytotoxic drug to an antibody improves the therapeutic index", Nature Biotechnology, vol. 26, No. 8, pp. 925-932 (2008).

Ma, D. et al., "Potent Antitumor Activity of an Auristatin-Conjugated, Fully Human Monoclonal Antibody to Prostate-Specific Membrane Antigen", Clin. Cancer Res., vol. 12, No. 8, pp. 2591-2596 (2006).

Messerschmidt, S.K.E. et al., "Novel Single-Chain Fv' Formats for the Generation of lmmunoliposomes by Site-Directed Coupling", Bioconjugate Chem., vol. 19, No. 1, pp. 362-369 (2008).

Rege, K. et al., "Amphipathic Peptide-Based Fusion Peptides and Immunoconjugates for the Targeted Ablation of Prostate Cancer Cells", Cancer Res., vol. 67, No. 13, pp. 6368-6375 (2007).

Wang, D. et al., "Generation and Characterization of an Anti-CD19 Single-Chain Fv Immunotoxin Composed of C-Terminal Disulfide-Linked dgRTA", Bioconjugate Chem., vol. 8, No. 6, pp. 878-884 (1997).

\* cited by examiner

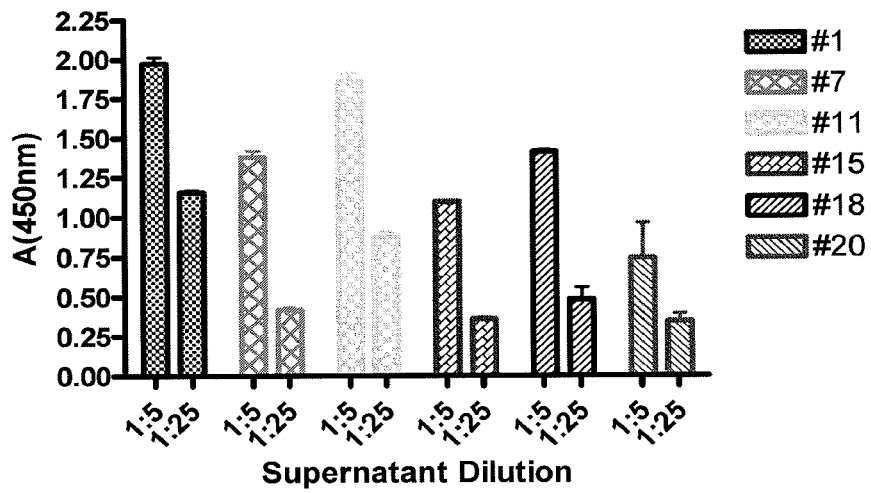
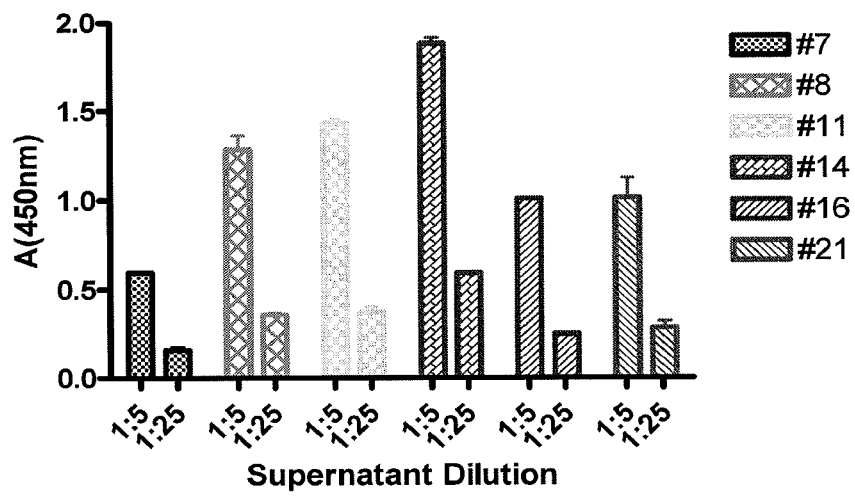
FIGURE 3

```
                              1                                                50
2A10 HC CDS  aa     (1)  MRAWIFFLLCLAGRALAEVQLVQSGAEVKKPGESLKISCKGSGYSFTSNW
2A10 HC CAA  aa     (1)  MRAWIFFLLCLAGRALAEVQLVQSGAEVKKPGESLKISCKGSGYSFTSNW
2A10 HC C442 aa     (1)  MRAWIFFLLCLAGRALAEVQLVQSGAEVKKPGESLKISCKGSGYSFTSNW 51                                               100
2A10 HC CDS  aa    (51)  IGWVRQMPGKGLEWMGIIYPGDSDTRYSPSFQGQVTISADKSISTAYLQW
2A10 HC CAA  aa    (51)  IGWVRQMPGKGLEWMGIIYPGDSDTRYSPSFQGQVTISADKSISTAYLQW
2A10 HC C442 aa    (51)  IGWVRQMPGKGLEWMGIIYPGDSDTRYSPSFQGQVTISADKSISTAYLQW 101                                              150
2A10 HC CDS  aa   (101)  SSLKASDTAMYYCARQTGFLWSSDLWGRGTLVTVSSASTKGPSVFPLAPS
2A10 HC CAA  aa   (101)  SSLKASDTAMYYCARQTGFLWSSDLWGRGTLVTVSSASTKGPSVFPLAPS
2A10 HC C442 aa   (101)  SSLKASDTAMYYCARQTGFLWSSDLWGRGTLVTVSSASTKGPSVFPLAPS 151                                              200
2A10 HC CDS  aa   (151)  SKSTSGGTAALGCLVKDYFPEPVTVSWNSGALTSGVHTFPAVLQSSGLYS
2A10 HC CAA  aa   (151)  SKSTSGGTAALGCLVKDYFPEPVTVSWNSGALTSGVHTFPAVLQSSGLYS
2A10 HC C442 aa   (151)  SKSTSGGTAALGCLVKDYFPEPVTVSWNSGALTSGVHTFPAVLQSSGLYS 201                                              250
2A10 HC CDS  aa   (201)  LSSVVTVPSSSLGTQTYICNVNHKPSNTKVDKRVEPKSCDKTHTCPPCPA
2A10 HC CAA  aa   (201)  LSSVVTVPSSSLGTQTYICNVNHKPSNTKVDKRVEPKSCDKTHTCPPCPA
2A10 HC C442 aa   (201)  LSSVVTVPSSSLGTQTYICNVNHKPSNTKVDKRVEPKSCDKTHTCPPCPA 251                                              300
2A10 HC CDS  aa   (251)  PELLGGPSVFLFPPKPKDTLMISRTPEVTCVVVDVSHEDPEVKFNWYVDG
2A10 HC CAA  aa   (251)  PELLGGPSVFLFPPKPKDTLMISRTPEVTCVVVDVSHEDPEVKFNWYVDG
2A10 HC C442 aa   (251)  PELLGGPSVFLFPPKPKDTLMISRTPEVTCVVVDVSHEDPEVKFNWYVDG 301                                              350
2A10 HC CDS  aa   (301)  VEVHNAKTKPREEQYNSTYRVVSVLTVLHQDWLNGKEYKCKVSNKALPAP
2A10 HC CAA  aa   (301)  VEVHNAKTKPREEQYNSTYRVVSVLTVLHQDWLNGKEYKCKVSNKALPAP
2A10 HC C442 aa   (301)  VEVHNAKTKPREEQYNSTYRVVSVLTVLHQDWLNGKEYKCKVSNKALPAP 351                                              400
2A10 HC CDS  aa   (351)  IEKTISKAKGQPREPQVYTLPPSREEMTKNQVSLTCLVKGFYPSDIAVEW
2A10 HC CAA  aa   (351)  IEKTISKAKGQPREPQVYTLPPSREEMTKNQVSLTCLVKGFYPSDIAVEW
2A10 HC C442 aa   (351)  IEKTISKAKGQPREPQVYTLPPSREEMTKNQVSLTCLVKGFYPSDIAVEW 401                                              450
2A10 HC CDS  aa   (401)  ESNGQPENNYKTTPPVLDSDGSFFLYSKLTVDKSRWQQGNVFSCSVMHEA
2A10 HC CAA  aa   (401)  ESNGQPENNYKTTPPVLDSDGSFFLYSKLTVDKSRWQQGNVFSCSVMHEA
2A10 HC C442 aa   (401)  ESNGQPENNYKTTPPVLDSDGSFFLYSKLTVDKSRWQQGNVFSCSVMHEA 451            470
2A10 HC CDS  aa   (451)  LHNHYTQKSLSLSPGK----
2A10 HC CAA  aa   (451)  LHNHYTQKSLSLSPGKCAA-
2A10 HC C442 aa   (451)  LHNHYTQKSLCLSPGK----
```

FIGURE 4

|  |  | 1 | 50 |
|---|---|---|---|
| 2A10 HC CDS | (1) | ATGAGGGCTTGGATCTTCTTTCTGCTCTGCCTGGCCGGGAGAGCGCTCGC | |
| 2A10 HC CAA | (1) | ATGAGGGCTTGGATCTTCTTTCTGCTCTGCCTGGCCGGGAGAGCGCTCGC | |
| 2A10 HC C442 | (1) | ATGAGGGCTTGGATCTTCTTTCTGCTCTGCCTGGCCGGGAGAGCGCTCGC | |
|  |  | 51 | 100 |
| 2A10 HC CDS | (51) | AGAGGTGCAGCTGGTGCAGTCTGGAGCAGAGGTGAAAAAGCCCGGGGAGT | |
| 2A10 HC CAA | (51) | AGAGGTGCAGCTGGTGCAGTCTGGAGCAGAGGTGAAAAAGCCCGGGGAGT | |
| 2A10 HC C442 | (51) | AGAGGTGCAGCTGGTGCAGTCTGGAGCAGAGGTGAAAAAGCCCGGGGAGT | |
|  |  | 101 | 150 |
| 2A10 HC CDS | (101) | CTCTGAAGATCTCCTGTAAGGGTTCTGGATACAGCTTTACCAGTAACTGG | |
| 2A10 HC CAA | (101) | CTCTGAAGATCTCCTGTAAGGGTTCTGGATACAGCTTTACCAGTAACTGG | |
| 2A10 HC C442 | (101) | CTCTGAAGATCTCCTGTAAGGGTTCTGGATACAGCTTTACCAGTAACTGG | |
|  |  | 151 | 200 |
| 2A10 HC CDS | (151) | ATCGGCTGGGTGCGCCAGATGCCCGGGAAAGGCCTGGAGTGGATGGGGAT | |
| 2A10 HC CAA | (151) | ATCGGCTGGGTGCGCCAGATGCCCGGGAAAGGCCTGGAGTGGATGGGGAT | |
| 2A10 HC C442 | (151) | ATCGGCTGGGTGCGCCAGATGCCCGGGAAAGGCCTGGAGTGGATGGGGAT | |
|  |  | 201 | 250 |
| 2A10 HC CDS | (201) | CATCTATCCTGGTGACTCTGATACCAGATACAGCCCGTCCTTCCAAGGCC | |
| 2A10 HC CAA | (201) | CATCTATCCTGGTGACTCTGATACCAGATACAGCCCGTCCTTCCAAGGCC | |
| 2A10 HC C442 | (201) | CATCTATCCTGGTGACTCTGATACCAGATACAGCCCGTCCTTCCAAGGCC | |
|  |  | 251 | 300 |
| 2A10 HC CDS | (251) | AGGTCACCATCTCAGCCGACAAGTCCATCAGCACCGCCTACCTGCAGTGG | |
| 2A10 HC CAA | (251) | AGGTCACCATCTCAGCCGACAAGTCCATCAGCACCGCCTACCTGCAGTGG | |
| 2A10 HC C442 | (251) | AGGTCACCATCTCAGCCGACAAGTCCATCAGCACCGCCTACCTGCAGTGG | |
|  |  | 301 | 350 |
| 2A10 HC CDS | (301) | AGCAGCCTGAAGGCCTCGGACACCGCCATGTATTACTGTGCGAGGCAAAC | |
| 2A10 HC CAA | (301) | AGCAGCCTGAAGGCCTCGGACACCGCCATGTATTACTGTGCGAGGCAAAC | |
| 2A10 HC C442 | (301) | AGCAGCCTGAAGGCCTCGGACACCGCCATGTATTACTGTGCGAGGCAAAC | |
|  |  | 351 | 400 |
| 2A10 HC CDS | (351) | TGGTTTCCTCTGGTCCTCCGATCTCTGGGGCCGTGGCACCCTGGTCACTG | |
| 2A10 HC CAA | (351) | TGGTTTCCTCTGGTCCTCCGATCTCTGGGGCCGTGGCACCCTGGTCACTG | |
| 2A10 HC C442 | (351) | TGGTTTCCTCTGGTCCTCCGATCTCTGGGGCCGTGGCACCCTGGTCACTG | |
|  |  | 401 | 450 |
| 2A10 HC CDS | (401) | TCTCCTCAGCTAGCACCAAGGGCCCATCGGTCTTCCCCCTGGCACCCTCC | |
| 2A10 HC CAA | (401) | TCTCCTCAGCTAGCACCAAGGGCCCATCGGTCTTCCCCCTGGCACCCTCC | |
| 2A10 HC C442 | (401) | TCTCCTCAGCTAGCACCAAGGGCCCATCGGTCTTCCCCCTGGCACCCTCC | |
|  |  | 451 | 500 |
| 2A10 HC CDS | (451) | TCCAAGAGCACCTCTGGGGGCACAGCGGCCCTGGGCTGCCTGGTCAAGGA | |
| 2A10 HC CAA | (451) | TCCAAGAGCACCTCTGGGGGCACAGCGGCCCTGGGCTGCCTGGTCAAGGA | |
| 2A10 HC C442 | (451) | TCCAAGAGCACCTCTGGGGGCACAGCGGCCCTGGGCTGCCTGGTCAAGGA | |
|  |  | 501 | 550 |
| 2A10 HC CDS | (501) | CTACTTCCCCGAACCGGTGACGGTGTCGTGGAACTCAGGCGCCCTGACCA | |
| 2A10 HC CAA | (501) | CTACTTCCCCGAACCGGTGACGGTGTCGTGGAACTCAGGCGCCCTGACCA | |
| 2A10 HC C442 | (501) | CTACTTCCCCGAACCGGTGACGGTGTCGTGGAACTCAGGCGCCCTGACCA | |
|  |  | 551 | 600 |
| 2A10 HC CDS | (551) | GCGGCGTGCACACCTTCCCGGCTGTCCTACAGTCCTCAGGACTCTACTCC | |
| 2A10 HC CAA | (551) | GCGGCGTGCACACCTTCCCGGCTGTCCTACAGTCCTCAGGACTCTACTCC | |
| 2A10 HC C442 | (551) | GCGGCCTCCACACCTTCCCGGCTGTCCTACAGTCCTCAGGACTCTACTCC | |
|  |  | 601 | 650 |
| 2A10 HC CDS | (601) | CTCAGCAGCGTGGTGACCGTGCCCTCCAGCAGCTTGGGCACCCAGACCTA | |
| 2A10 HC CAA | (601) | CTCAGCAGCGTGGTGACCGTGCCCTCCAGCAGCTTGGGCACCCAGACCTA | |
| 2A10 HC C442 | (601) | CTCAGCAGCGTGGTGACCGTGCCCTCCAGCAGCTTGGGCACCCAGACCTA | |
|  |  | 651 | 700 |
| 2A10 HC CDS | (651) | CATCTGCAACGTGAATCACAAGCCCAGCAACACCAAGGTGGACAAGAGAG | |
| 2A10 HC CAA | (651) | CATCTGCAACGTGAATCACAAGCCCAGCAACACCAAGGTGGACAAGAGAG | |
| 2A10 HC C442 | (651) | CATCTGCAACGTGAATCACAAGCCCAGCAACACCAAGGTGGACAAGAGAG | |

FIGURE 5A

| | | |
|---|---|---|
| 2A10 HC CDS | (701) | TTGAGCCCAAATCTTGTGACAAAACTCACACATGCCCACCGTGCCCAGCA |
| 2A10 HC CAA | (701) | TTGAGCCCAAATCTTGTGACAAAACTCACACATGCCCACCGTGCCCAGCA |
| 2A10 HC C442 | (701) | TTGAGCCCAAATCTTGTGACAAAACTCACACATGCCCACCGTGCCCAGCA |
| | | 751                                             800 |
| 2A10 HC CDS | (751) | CCTGAACTCCTGGGGGGACCGTCAGTCTTCCTCTTCCCCCCAAAACCCAA |
| 2A10 HC CAA | (751) | CCTGAACTCCTGGGGGGACCGTCAGTCTTCCTCTTCCCCCCAAAACCCAA |
| 2A10 HC C442 | (751) | CCTGAACTCCTGGGGGGACCGTCAGTCTTCCTCTTCCCCCCAAAACCCAA |
| | | 801                                             850 |
| 2A10 HC CDS | (801) | GGACACCCTCATGATCTCCCGGACCCCTGAGGTCACATGCGTGGTGGTGG |
| 2A10 HC CAA | (801) | GGACACCCTCATGATCTCCCGGACCCCTGAGGTCACATGCGTGGTGGTGG |
| 2A10 HC C442 | (801) | GGACACCCTCATGATCTCCCGGACCCCTGAGGTCACATGCGTGGTGGTGG |
| | | 851                                             900 |
| 2A10 HC CDS | (851) | ACGTGAGCCACGAAGACCCTGAGGTCAAGTTCAACTGGTACGTGGACGGC |
| 2A10 HC CAA | (851) | ACGTGAGCCACGAAGACCCTGAGGTCAAGTTCAACTGGTACGTGGACGGC |
| 2A10 HC C442 | (851) | ACGTGAGCCACGAAGACCCTGAGGTCAAGTTCAACTGGTACGTGGACGGC |
| | | 901                                             950 |
| 2A10 HC CDS | (901) | GTGGAGGTGCATAATGCCAAGACAAAGCCGCGGGAGGAGCAGTACAACAG |
| 2A10 HC CAA | (901) | GTGGAGGTGCATAATGCCAAGACAAAGCCGCGGGAGGAGCAGTACAACAG |
| 2A10 HC C442 | (901) | GTGGAGGTGCATAATGCCAAGACAAAGCCGCGGGAGGAGCAGTACAACAG |
| | | 951                                            1000 |
| 2A10 HC CDS | (951) | CACGTACCGTGTGGTCAGCGTCCTCACCGTCCTGCACCAGGACTGGCTGA |
| 2A10 HC CAA | (951) | CACGTACCGTGTGGTCAGCGTCCTCACCGTCCTGCACCAGGACTGGCTGA |
| 2A10 HC C442 | (951) | CACGTACCGTGTGGTCAGCGTCCTCACCGTCCTGCACCAGGACTGGCTGA |
| | | 1001                                           1050 |
| 2A10 HC CDS | (1001) | ATGGCAAGGAGTACAAGTGCAAGGTCTCCAACAAAGCCCTCCCAGCCCCC |
| 2A10 HC CAA | (1001) | ATGGCAAGGAGTACAAGTGCAAGGTCTCCAACAAAGCCCTCCCAGCCCCC |
| 2A10 HC C442 | (1001) | ATGGCAAGGAGTACAAGTGCAAGGTCTCCAACAAAGCCCTCCCAGCCCCC |
| | | 1051                                           1100 |
| 2A10 HC CDS | (1051) | ATCGAGAAAACCATCTCCAAAGCCAAAGGGCAGCCCCGAGAACCACAGGT |
| 2A10 HC CAA | (1051) | ATCGAGAAAACCATCTCCAAAGCCAAAGGGCAGCCCCGAGAACCACAGGT |
| 2A10 HC C442 | (1051) | ATCGAGAAAACCATCTCCAAAGCCAAAGGGCAGCCCCGAGAACCACAGGT |
| | | 1101                                           1150 |
| 2A10 HC CDS | (1101) | GTACACCCTGCCCCCATCCCGGGAGGAGATGACCAAGAACCAGGTCAGCC |
| 2A10 HC CAA | (1101) | GTACACCCTGCCCCCATCCCGGGAGGAGATGACCAAGAACCAGGTCAGCC |
| 2A10 HC C442 | (1101) | GTACACCCTGCCCCCATCCCGGGAGGAGATGACCAAGAACCAGGTCAGCC |
| | | 1151                                           1200 |
| 2A10 HC CDS | (1151) | TGACCTGCCTGGTCAAAGGCTTCTATCCCAGCGACATCGCCGTGGAGTGG |
| 2A10 HC CAA | (1151) | TGACCTGCCTGGTCAAAGGCTTCTATCCCAGCGACATCGCCGTGGAGTGG |
| 2A10 HC C442 | (1151) | TGACCTGCCTGGTCAAAGGCTTCTATCCCAGCGACATCGCCGTGGAGTGG |
| | | 1201                                           1250 |
| 2A10 HC CDS | (1201) | GAGAGCAATGGGCAGCCGGAGAACAACTACAAGACCACGCCTCCCGTGCT |
| 2A10 HC CAA | (1201) | GAGAGCAATGGGCAGCCGGAGAACAACTACAAGACCACGCCTCCCGTGCT |
| 2A10 HC C442 | (1201) | GAGAGCAATGGGCAGCCGGAGAACAACTACAAGACCACGCCTCCCGTGCT |
| | | 1251                                           1300 |
| 2A10 HC CDS | (1251) | GGACTCCGACGGCTCCTTCTTCCTCTATAGCAAGCTCACCGTGGACAAGA |
| 2A10 HC CAA | (1251) | GGACTCCGACGGCTCCTTCTTCCTCTATAGCAAGCTCACCGTGGACAAGA |
| 2A10 HC C442 | (1251) | GGACTCCGACGGCTCCTTCTTCCTCTATAGCAAGCTCACCGTGGACAAGA |
| | | 1301                                           1350 |
| 2A10 HC CDS | (1301) | GCAGGTGGCAGCAGGGGAACGTCTTCTCATGCTCCGTGATGCATGAGGCT |
| 2A10 HC CAA | (1301) | GCAGGTGGCAGCAGGGGAACGTCTTCTCATGCTCCGTGATGCATGAGGCT |
| 2A10 HC C442 | (1301) | GCAGGTGGCAGCAGGGGAACGTCTTCTCATGCTCCGTGATGCATGAGGCT |
| | | 1351                                           1400 |
| 2A10 HC CDS | (1351) | CTGCACAACCACTACACGCAGAAGAGCCTCTCCCTGTCCCCGGGTAAATG |
| 2A10 HC CAA | (1351) | CTGCACAACCACTACACGCAGAAGAGCCTCTCCCTGTCCCCGGGTAAATG |
| 2A10 HC C442 | (1351) | CTGCACAACCACTACACGCAGAAGAGCCTCTGCCTGTCCCCGGGTAAATG |
| | | 1401 |
| 2A10 HC CDS | (1401) | A-------- |
| 2A10 HC CAA | (1401) | TGCAGCTTGA |
| 2A10 HC C442 | (1401) | A-------- |

FIGURE 5B

SITE-SPECIFIC ATTACHMENT OF DRUGS OR OTHER AGENTS TO ENGINEERED ANTIBODIES WITH C-TERMINAL EXTENSIONS

CROSS-REFERENCE TO RELATED APPLICATIONS

This application claims priority to U.S. Provisional Patent Application No. 60/957,271 filed Aug. 22, 2007, which is incorporated by reference herein in its entirety.

FIELD OF THE INVENTION

The present invention provides antibodies having cysteine-containing C-terminal extensions facilitating conjugation to a wide variety of partner molecules, including drugs, radioisotopes, toxins, enymes, binding moieties, marker molecules, proteins and therapeutic agents.

BACKGROUND

Conjugates of antibodies with drugs, radioisotopes, and proteins have been widely investigated, and a range of chemical approaches are available and widely used. Conjugation is normally carried out to amino acid side chains, for example to lysine residues, in a random fashion such that a distribution of chemically modified species is found in each preparation of conjugate, where different positions in the antibody may be modified each time. Although successfully used, this approach has several disadvantages. These include the fact that amino acids important for function of the antibody, for example in antigen binding or Fc receptor binding, may be modified and consequently functionality of the antibody may be modified or lost. In addition, the heterogeneity of the antibody conjugate in which a population of molecules exists with different side chains modified complicates analysis and makes it difficult to ensure that each preparation contains the same distribution of modified species.

A potential improvement to conjugation is to attach the drug or other molecule at a specific site, which is identical each time. This can be designed such that attachment to the site does not interfere with antibody functional properties, and allows simplified analysis and quality control of conjugate preparations. A number of approaches have been used to accomplish this either using naturally occurring sites in the antibody molecule or by specifically introducing additional sites through antibody engineering.

The generation of free cysteines by selective reduction of the hinge region has been used for the attachment of thiol reactive compounds to both IgG and antibody fragments, for example, to attach fluorescent compounds (Packard et al., Biochem. 25, 3548-3552 (1986)), for attachment of chelators that can be used for site-specific radiolabelling (King et al., Cancer Res., 54, 6176-6185 (1994)), and for drug attachment (Doronina et al., Nature Biotechnol. 21, 778-784 (2003)). Disadvantages of this approach include the reduction of disulfide bonds which are important for maintenance of the native antibody structure. This may have detrimental effects on the functionality or stability of the resulting conjugate. Also, as several disulfide bonds are present in the antibody molecule, including two in the hinge region for human IgG1, one attaching each light chain to heavy chain, and one internal disulfide in each folded immunoglobulin domain, there remains potential heterogeneity in the conjugate produced.

The Fc region carbohydrate also provides a natural specific attachment site for IgG molecules. The carbohydrate is usually modified by periodate oxidation to generate reactive aldehydes which can then be used to attach reactive amine containing compounds by Schiff base formation. As the aldehydes can react with amine groups, reactions are carried out at low pH so that the lysine residues are protonated and unreactive. Hydrazide groups are most suitable for attachment to the aldehydes generated since they are reactive at low pH to form a hydrazone linkage. The linkage can then be further stabilized by reduction with sodium cyanoborohydride to form a hydrazine linkage (Rodwell et al., Proc. Natl. Acad. Sci. (USA) 83, 2632-2636 (1986)). The disadvantages of this approach are the relatively harsh conditions required which can damage and aggregate some antibody molecules. Methionine residues present in some antibody variable regions may be particularly susceptible to oxidation by periodate which can lead to loss of antigen binding avidity. In some cases histidine or tryptophan residues might also be affected.

Antibody engineering can be used to introduce specific attachment sites into antibody molecules, and this can be incorporated as part of the design of an engineered molecule. Extra cysteine residues can be introduced onto the surface of antibody constant domains to provide a specific attachment site without the need to disrupt native disulphide bonds. Introduction of specific cysteine residues in the CH1 domain of the IgG heavy chain has been shown to result in sites to which ligands can be attached without any loss of antigen binding (Lyons et al., Protein Engin. 3, 703-708 (1990)). These mutations can be used to produce site-specifically labeled IgG or Fab antibody fragments (Bodmer et al., U.S. Pat. No. 5,219, 996). Similar work to produce site-specific drug conjugates has recently been reported by Genentech (Eigenbrot et al., U.S. Patent Publication No. 2007/0092940).

Mutations in the Fc region of the antibody have also been explored. Substitution of a serine residue near the C-terminus of the CH3 domain (Ser444) to cysteine resulted in the production of IgG dimer of a chimeric human IgG1. This mutation resulted in 50% of the molecules forming dimeric IgG (Shopes, 1992). The same mutation introduced into a humanized IgG1 also resulted in the formation of IgG dimers (Caron et al., J. Exp. Med. 176, 1191-1195 (1992)). An alternative mutation in the Fc region at position 442 has also been generated and used for site-specific attachment (Stimmel et al., J. Biol. Chem. 275, 30445-30450 (2000)).

Antibody fragments such as single-chain Fv and diabodies have been engineered in which an extra cysteine residue is added at the C-terminus of the molecule (e.g. Cumber et al., J. Immunol. 149, 120-126 (1992); King et al, Cancer Res., 54, 6176-6185 (1994); L[1] et al., Bioconjugate Chem. 13, 985-995 (2002); Yang et al., Protein Engineering 16, 761-770 (2003); Olafson et al., Protein Engineering Design & Selection, 17, 21-27 (2004)).

Alternative methods for site-specific attachment include the introduction of extra glycosylation sites to allow attachment via periodate oxidation. Some antibody light chains have an unusual natural glycosylation site, and thus the light chain has been used as a site to introduce a glycosylation site into antibodies which do not normally have a carbohydrate attached to the light chain (Leung et al., J. Immunol. 154, 5919-5926 (1995)). A third engineering strategy is to introduce extra lysine residues into the surface of the constant region domains (Hemminki et al., Protein Engin. 8, 185-191 (1995)). Although this approach does not introduce a unique labeling site, lysine reactive reagents are more likely to modify the antibody at the increased concentration of lysine residues in the constant region resulting in the retention of more antigen binding reactivity.

A more specialized approach is the use of reverse proteolysis to attach reagents specifically at the C-terminus of Fab' heavy chains (Fisch et al., Bioconj. Chem. 3, 147-153 (1992)). After production of a F(ab')2 fragment by the protease lysyl endopeptidase, experimental conditions can be altered such that the same protease working in reverse is capable of the specific attachment of carbohydrazide groups to the C-terminus of the F(ab')2 heavy chains. These carbohydrazide groups could then be used as an attachment point for a radiolabelled chelator reacting via an aldehyde group to form a hydrazone linkage.

Despite the background art described above, there remains a need to conjugate partner molecules (e.g. a drug or toxin) to intact IgG molecules, which are better characterized and more stable than antibody fragments. The potential benefits of attachment of partner molecules to the IgG instead of antibody fragments include retention of Fc region dependent effector functions, such as Fc receptor-dependent ADCC and phagocytosis, and also retention of the FcRn binding site which allows a long serum half-life to be maintained. As described in detail below, the instant invention satisfies this need.

SUMMARY OF THE INVENTION

The present invention provides antibodies (e.g., IgG antibodies) having C-terminal cysteine-containing extensions that facilitate antibody conjugation to a partner molecule (e.g. a drug, toxin, marker molecule, protein, radioisotope, or other therapeutic agent).

In one embodiment, the antibody-partner molecule conjugate comprises a full-length antibody conjugated to a partner molecule wherein the conjugation occurs via a cysteine-containing extension at the C-terminus of a heavy chain of the antibody.

In some aspects of the invention, the antibody-partner molecule conjugate is made by adding a cysteine-containing extension to the heavy chain of the antibody.

In other aspects of the invention, the antibody-partner molecule is made by replacing the original C-terminal amino acid residue of the heavy chain of the antibody with C-terminal cysteine-containing extension.

In some embodiments, the partner molecule of the antibody-partner molecule conjugate is a drug. In some aspects, the drug is a cytotoxic drug.

In some aspects of the invention, the cytotoxic drug is selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid.

In some aspects of the invention, the cytotoxic drug is formula (m), formula (n), AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, dolastatin-10, echinomycin, combretatstatin, chalicheamicin, maytansine, DM-1, or netropsin.

In some aspects of the invention, the cytotoxic drug is an anti-tubulin agent. In some embodiments, the anti-tubulin agent is an auristatin, a vinca alkaloid, a podophyllotoxin, a taxane, a baccatin derivative, a cryptophysin, a maytansinoid, a combretastatin, or a dolastatin. In other aspects of the invention, the antitubulin agent is AFP, MMAF, MMAE, AEB, AEVB, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodennolide, maytansine, DM-1, or eleutherobin.

In other aspects of the invention, the cytotoxic drug of the antibody-partner molecule conjugate is gancyclovir, etanercept, cyclosporine, tacrolimus, rapamycin, cyclophosphamide, azathioprine, mycophenolate mofetil, methotrexate, cortisol, aldosterone, dexamethasone, a cyclooxygenase inhibitor, a 5-ipoxygenase inhibitor, or a leukotriene receptor antagonist.

In some embodiments of the invention, the antibody-partner molecule conjugate of the invention comprises a C-terminal cysteine-containing extension having an amino acid sequence selected from a CAA C-terminal extension, a CCAA (SEQ ID NO:9) C-terminal extension, a AACAA (SEQ ID NO:7) C-terminal extension, or a GGGGSCAA (SEQ ID NO:8) C-terminal extension of the antibody.

In some embodiments, the antibody-partner molecule conjugate of the invention comprises a linker. In some aspects of the invention the linker is cleavable under intracellular conditions. In some aspects of the invention, peptide linker is cleavable by an intracellular protease. The antibody-partner molecule conjugate of claim 14, wherein the intracellular protease is a lysosomal protease or an endosomal protease.

In some embodiments if the invention, the peptide linker of the antibody-partner molecule conjugate is a dipeptide linker. In some aspects of the invention, the dipeptide linker is a val-cit linker or a phe-lys linker.

In some embodiments, the cleavable linker of the partner molecule conjugate is hydrolyzable at a pH of less than 5.5. In some aspects of the invention, the hydrolyzable linker is a hydrazone linker. In other aspects of the invention, the cleavable linker is a disulfide linker.

In some embodiments, the antibody-drug conjugate of the invention comprises:
a full length antibody that:
(a) binds to PSMA, and
(b) is conjugated to a cytotoxic agent or an immunosuppressive agent,
wherein the antibody-drug conjugate exerts:
(a) a cytotoxic or cytostatic effect on a PSMA-expressing cancer cell line, or
(b) a cytotoxic, cytostatic, or immunosuppressive effect on a PSMA-expressing immune cell,
wherein the conjugation occurs at a an introduced cysteine residue at or near the C-terminus of a heavy chain of the antibody.

Other aspects of the invention include a method of making an antibody-partner molecular conjugate, comprising the steps of:
(a) providing a full-length antibody;
(b) modifying the C-terminus of at least one of the heavy chains of the full-length antibody by adding thereto a cysteine-containing extension; and
(c) conjugating the modified full-length antibody to a partner molecule via the cysteine residue of the cysteine-containing extension.

Some aspects of the invention include the methods of making an antibody-partner molecular conjugate method wherein the cysteine-containing extension has an amino acid sequence selected from a group consisting of CAA, CCAA (SEQ ID NO:9), AACAA (SEQ ID NO:7), and GGGGSCAA (SEQ ID NO:8).

Some embodiments of the invention provide methods of preparing an antibody for use in an antibody-partner molecular conjugate, comprising the steps of:
(a) providing a full-length antibody; and
(b) modifying the C-terminus of at least one of the heavy chains of the full-length antibody by adding thereto a cysteine-containing extension.

In some aspects, the methods are for preparing antibody for use in an antibody-partner molecular conjugate, wherein the cysteine-containing extension of the antibody has an amino acid sequence selected from the group consisting of CAA, CCAA (SEQ ID NO:9), AACAA (SEQ ID NO:7), and GGGGSCAA (SEQ ID NO:8).

Other embodiments of the invention provide a full length antibody, wherein the C-terminus of at least one of its heavy chains has been modified by adding thereto a cysteine-containing extension.

Some aspects of the invention are methods for the treatment of a PSMA-expressing cancer in a subject, the method comprising: administering to the subject, in an amount effective for the treatment, an antibody-drug conjugate comprising a full length antibody that binds to PSMA and wherein the drug is a cytotoxic or cytostatic agent, and the drug is conjugated to the antibody at a cysteine residue at the C-terminus of a heavy chain of the antibody.

BRIEF DESCRIPTION OF THE DRAWINGS

FIG. 3: 2A10-CAA and 2A10-C442 ELISA Results. Human IgG expression by 2A10 LC 153-117, 2A10 HC CAA 153-118 and 2A10 HC C442 153-118 constructs.

FIG. 4: 2A10 Amino Acid Sequences. Comparison of the amino acid sequences of 2A10 (SEQ ID NO:1), 2A10-CAA (SEQ ID NO:2), and 2A10-C442 (SEQ ID NO:3).

FIG. 5: 2A10 Nucleic Acid Sequences. Comparison of the nucleic acid sequences of 2A10 (SEQ ID NO:4), 2A10-CAA (SEQ ID NO:5), and 2A10-C442 (SEQ ID NO:6).

DETAILED DESCRIPTION

Definitions

Figure 1:
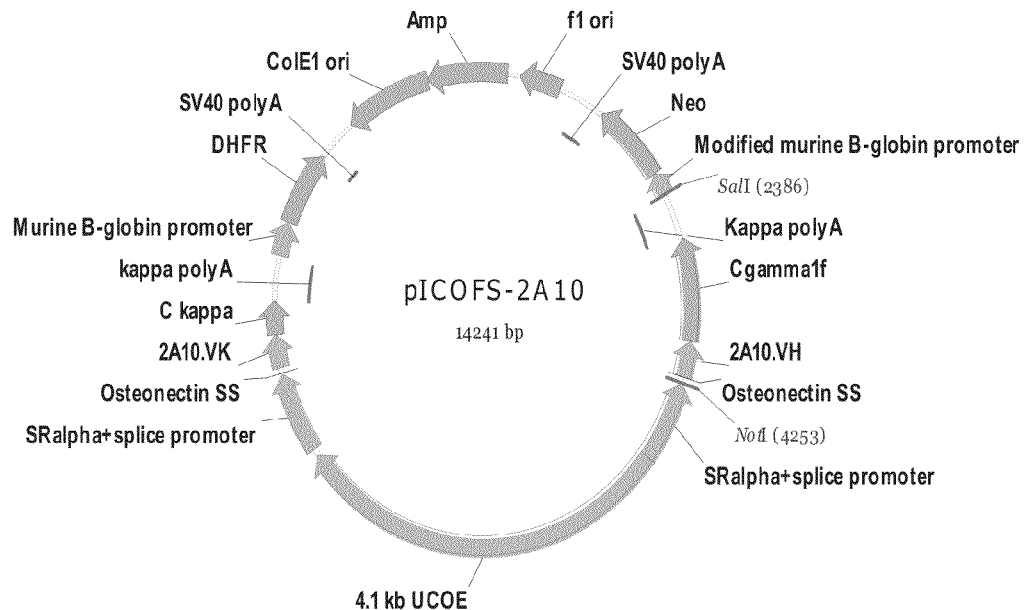
FIG. 1: pICOFs-2A10 plasmid. Starting vector pICOFs-2A10.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "therapeutic agent" is intended to mean a compound that, when present in a therapeutically effective amount, produces a desired therapeutic effect on a mammal. For certain indications (e.g. for treating carcinomas) it is desirable that the therapeutic agent also be capable of entering the target cell.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

The term "cytotoxin" is intended to mean a therapeutic agent having the desired effect of being cytotoxic to cancer cells. Cytotoxic means that the agent arrests the growth of, or kills the cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analogues, calicheamicins, doxorubicin, auristatins and maytansinoids.

The term "marker" is intended to mean a compound useful in the characterization of tumors or other medical condition, for example, diagnosis, progression of a tumor, and assay of the factors secreted by tumor cells. Markers are considered a subset of "diagnostic agents."

The term "selective" as used in connection with enzymatic cleavage means that the rate of rate of cleavage of the linker moiety is greater than the rate of cleavage of a peptide having a random sequence of amino acids.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. These terms also encompass the term "antibody." The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH($NH_2$)—$CH_3$, and so forth.

Amino acids and peptides may be protected by blocking groups. A blocking group is an atom or a chemical moiety that protects the N-terminus of an amino acid or a peptide from undesired reactions and can be used during the synthesis of a drug-cleavable substrate conjugate. It should remain attached to the N-terminus throughout the synthesis, and may be removed after completion of synthesis of the drug conjugate by chemical conditions, enzymatic cleavage or other conditions that selectively achieve its removal. The blocking groups suitable for N-terminus protection are well known in the art of peptide chemistry. Exemplary blocking groups include, but are not limited to, hydrogen, D-amino acid, and carbobenzoxy (Cbz) chloride.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260: 2605-2608 (1985); Rossolini et al., Mol. Cell. Probes 8: 91-98 (1994)). The term nucleic acid is used interchangeably with gene, cDNA, mRNA, oligonucleotide, and polynucleotide.

The symbol "—", whether utilized as a bond or displayed perpendicular to a bond, indicates the point at which the displayed moiety is attached to the remainder of the molecule, solid support, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, and S, and wherein the nitrogen, carbon and sulfur atoms may optionally be oxidized and the nitrogen heteroatom may optionally be quaternized. The heteroatom(s) O, N, S, and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R"', —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R''')=NR"", —NR—C(NR'R")=NR"', —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R''' and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R"" groups when more than one of these groups is present. When R' and R" are attached to the same nitrogen atom, they can be combined with the nitrogen atom to form a 5, 6, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''' and R"" are preferably independently selected from hydrogen, ($C_1$-$C_8$)alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R''' and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. Substituents R, R', R" and R'" are preferably independently selected from hydrogen or substituted or unsubstituted (C$_1$-C$_6$) alkyl.

As used herein, the term "diphosphate" includes but is not limited to an ester of phosphoric acid containing two phosphate groups. The term "triphosphate" includes but is not limited to an ester of phosphoric acid containing three phosphate groups. For example, particular drugs having a diphosphate or a triphosphate include:

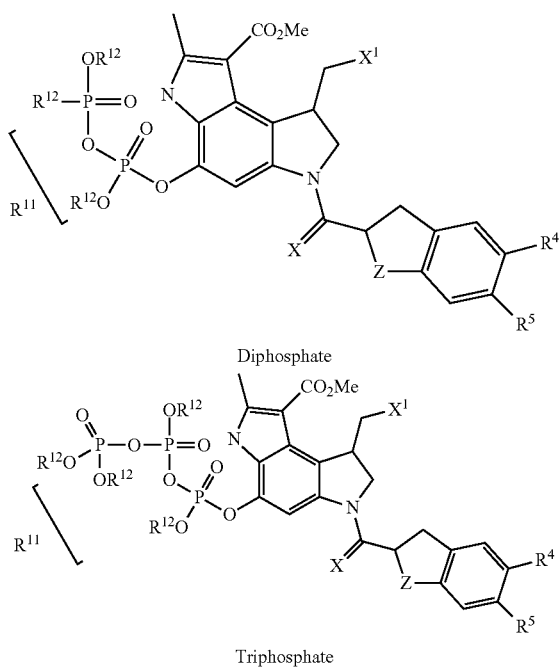

Diphosphate

Triphosphate

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

Unless specified otherwise, the term "antibody" refers to a protein, including a glycoprotein, of the immunoglobulin class comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH$_1$, CH$_2$ and CH$_3$. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3$^{rd}$ ed. 1993); (iv) a Fd fragment consisting of the VH and CH1 domains; (v) a Fv fragment consisting of the VL and VH domains of a single arm of an antibody, (vi) a dAb fragment (Ward et al., (1989) Nature 341:544-546), which consists of a VH domain; (vii) an isolated complementarity determining region (CDR); and (viii) a nanobody, a heavy chain variable region containing a single variable domain and two constant domains. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds a target antigen that is substantially free of antibodies that specifically bind antigens other than the target). An isolated antibody that specifically binds the target may, however, have cross-reactivity to other antigens, such as target molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "antibody derivative" refers to antibodies having mutated amino acid sequences, as compared to its germline sequence, where such mutations include substitutions, deletions, and insertions of amino acids. This term also refers to antibodies having post-translational modifications including, but not limited to, glycosylation, acylation, alkylation, amidation, biotinylation, lipoylation (e.g., as prenylation, myristoylation, and farnesylations), and PEGylation, as well as the addition of linker molecules, such as those described in detail below and those known in the art.

The terms "antibody conjugate" and "antibody partner molecule conjugate" refer to a full-length antibody, i.e., an antibody comprising at least two heavy (H) chains and two light (L) chains inter-connected by disulfide bonds, that is conjugated to a partner molecule.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "C-terminal extension" refers to the addition of up to ten but preferably five or fewer amino acid residues, preferably composed of small hydrophobic amino acids to the C-terminus of an antibody chain. In some embodiments, the C-terminal extension adds one or more terminal cysteine amino acid residues at or near the C-terminus to an antibody chain naturally lacking a cysteine residue within the five residues closest to the carboxyl terminus.

As used herein, an antibody that "specifically binds to a target" is intended to refer to an antibody that binds to a target with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "Kassoc" or "$K_a$," as used herein, is intended to refer to the association rate of a particular antibody-antigen interaction, whereas the term "Kdis" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

As used herein, the term "partner molecule" refers to the entity which is conjugated to an antibody in an antibody conjugate. Examples of partner molecules include drugs, toxins, marker molecules (e.g. radioisotopes), proteins and therapeutic agents.

Various aspects of the invention are described in further detail in the following subsections.

Antibodies which Form Conjugates with Partner Molecules

The antibody-partner molecule conjugates of the present invention include an antibody, (e.g., a monoclonal antibody, an antibody fragment, or an antibody derivative) that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. Poon et al., in the *Journal of Biological Chemistry*, 270:8571-8577 (1995), report the production of chimeric IgM antibodies.

Greenwood et al., in *Ther. Immunol.*, 1(5):247-55 (1994), report multiple-domain forms of the therapeutic monoclonal antibody CAMPATH-1H, including a homodimeric form of the antibody engineered by mutation of a serine residue to cysteine near the carboxy-terminal of the CH3 domain, resulting in improved lysis of target cells in a cytotoxicity assay.

Urnovitz et al., in U.S. Pat. No. 4,698,420, describe an antibody coupled to another moiety, e.g., a toxin such as ricin, via a naturally occurring cysteine residue in proximity to the carboxyl terminal end of the antibody heavy chain Barn et al., in U.S. Pat. No. 7,311,902, describe human interleukin-18 (IL-18) polypeptides and substitution mutants thereof conjugated to water-soluble polymers at specific sites on the human IL-18 protein via naturally occurring cysteine residues.

Kuau et al., in the *Journal of Biological Chemistry*, 269: 7610-7616 (1994), report the replacement of five surface exposed residues in *Pseudomonas* exotoxin A with cysteine residues for site-specific attachment of covalently bound polyethylene glycol (PEG).

Chilkoti et al., in *Bioconjugate Chem.*, 5:504-507 (1994), describe a cytochrome b5 molecule modified by site-directed mutagenesis to replace the threonine residue at position 8 with a cysteine residue for use in conjugating an active oligomer (N-isopropylacrylamide). The antibodies that are known in the art can be used in the conjugates of the invention, in particular for the treatment of the disease with which the target antigen is associated. Non-limiting examples of target antigens (and examples of their associated diseases) to which an antibody-partner molecule conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD70 (autoimmune diseases and cancer, including renal cell carcinoma), CD80 (psoriasis), CD23 (asthma), CD40L (immune thromobcy-topenic CTLA4 (T cell lymphomas) and BLys (autoimmune diseases, including systemic lupus erythematosus). Additional non-limiting examples of target antigens to which an antibody-partner molecule conjugate of the invention can be targeted include: CD19, Glypican-3, RG-1, MUC1, MUC16, TMPRSS4, Fibronectin ED-B, IRTA2, IRTA3, IRTA4, IRTA5, and Ephrin receptors.

Such antibodies are well known in the art and include, for example, antibodies to CD30 such as human monoclonal antibodies 17G1, 2H9 and 5E11, which are characterized and described in U.S. Patent Application Publication No. 2004/0006215. Additional non-limiting examples include monoclonal antibody 2A10 which specifically binds PSMA and is described in detail below, monoclonal antibodies 4C8, 4E10, 4E10.5, 5A8, 5C4, 5C4.1.3, 5D7, 5D7.1, 5E10, 5E10.12, 5G1, 5G1.4, 6A10, 6C9, 6C9.6, 6D9, 6D9.7, 6G4, 7E4, 7E4.4, 7E6, 7H8, 8E8, 8E8.4, 8F8, 8F8.19, 8H1, 9810, 9A10.1, 9B9, 9C1, 9G5, 105B, 10B5.8, 10B9, 10B9.2, 10D1, 10D1.3, 10E11, 10E4, 10E4.5, 11B4, 11D10, 11E4, 11E4.1, 11E8, 11E10, 11F11, 11F9, 11G1, 11G1.5, 1C7, 1H8.8, 2A7, 2A7.6, 2E2, 2E2.7, 2E7, 2E7.2, 2G1, 2G1.2, 3C12, 3E10, 3E10.5, 3E6, 3E6.0, 3F10, 4A1, 4B6 and 4B6.12 which specifically bind to CTLA-4 and are described in U.S. Patent Publication No. 20050201994, monoclonal antibodies 2G2, 2G5, 5A2, 7G8, 1E5, 4B7, and 7F5 which specifically bind IRTA5 and are described in US Patent Application Publication No. 20050266008, and monoclonal antibodies 2H5, 10B4, 8B5, 18E7 and 69A7 which specifically bind CD70 and are described in PCT Publication Nos. WO 2007/038637 and WO 2008/074004. Each of the patent publications cited are incorporated herein by reference in their entirety Other nonlimiting examples include monoclonal antibodies which specifically bind CD19, which are characterized and described in WO 2007/002223, monoclonal antibodies to B7H4, which are described in WO 2007/067991, monoclonal antibodies to PTK7, specifically described WO 2007/067730, monoclonal antibodies to RG1, which are described in U.S. Pat. No. 7,335,748, monoclonal antibodies to Mesothelin, which are described in U.S. Provisional Application Nos. 60/976,626 and 60/991,692, monoclonal antibodies to CD33, which are described in U.S. Pat. No. 7,342,110, monoclonal antibodies to CD30, which are described in U.S. Pat. No. 7,090,843, monoclonal antibodies to $CD_{20}$, which are described in U.S. Publication 2005/0180972, and monoclonal antibodies to C242, described in Kovtun et al., Cancer Res. 2006, 66, 3214-3221. Further included are monoclonal antibodies including Trastuzumab (Herceptin™), described in Beeram et al., J. Clin. Oncol. 26, 1028 (2008, May 20 Supp.), alemtuzumab, abciximab, biciromab (ReoPrO™.), omalizumab, BR96, eculizumab, MH-1, ATM-027, SC-1, bivatuzumab, BMS-188667, BMS-224818, SGN-15, CAT-213, J-695, rituximab (Rituxan™), CEA-Scan, sulesomab, palivizumab (Synagis™), basiliximab (Simulect™), daclizumab (Zenapax™), Oncolym™, CaroRx™, apolizumab, fontolizumab, Nuvion™, SMART anti-L-selectin Mab, TMA-15, YM-337, M60.1, WX-G250, Vitaxin™, mepolizumab, pascolizumab, tositumomab, efalizumab, 99 mTc-fanolesomab, metelimumab, CAL, MRA, MLN-2704, Onco-Rad PR356, liciliximab, MAb-81C6, clenoliximab, Melimmune™, HumaRAD16.88™, KW-2871, MLN-02, MDX-210, MDX-37, MDX-H210, 3F8, EMD-72000, SS (dsFv)PE38, infliximab (Remicade™), 111In-capromab pendetide; trastuzumab (Herceptin™), TNX-901, 5-D12, TheraCIM-h-R3™, TriAb, TRX-4, TriGem™, HRS-3/A9, BTI-322, siplizumab, Mycograb™, 1NG-1(heMAb), HepeX-B, pexelizumab, orgovomab, natalizumab, bevacizumab, cetuximab, epratuzumab, afelimomab, MDX-RA, inolimomab, lintuzumab, CeaVac™, mPA7, and mhoe-4.

Figure 10:
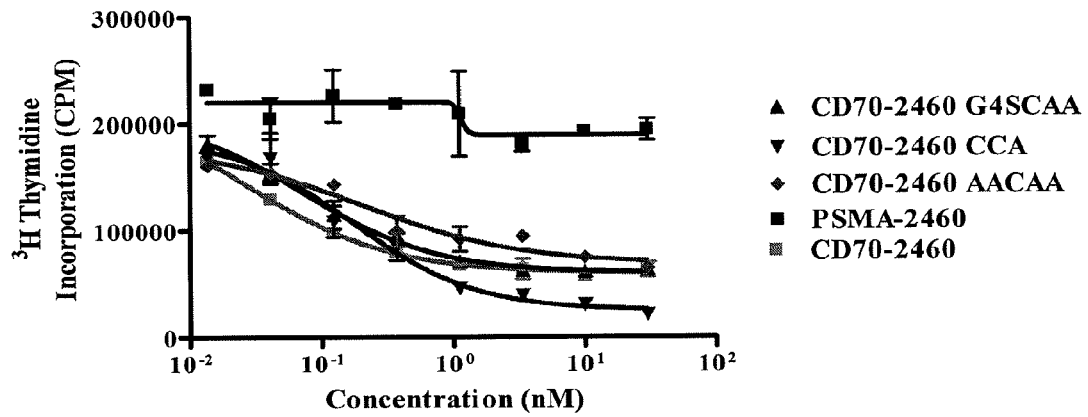
FIG. 10: Cytotoxicity assay. Assay monitoring cytotoxicity of formula (m)-conjugated antibodies.

In one embodiment of the instant invention, the antibody employed in the antibody-partner molecule conjugate specifically binds prostate-specific membrane antigen (PSMA) and is derived from the human antibody 2A10, the heavy chain sequence of which is presented in FIG. 10. In another embodiment the antibody employed in the antibody-partner molecule conjugate is derived from antibody 2A10 and includes a C-terminal cysteine amino acid residue. In a further embodiment the antibody employed in the antibody-partner molecule conjugate is derived from antibody 2A10 and includes a C-terminal Cys-Ala-Ala-extension to the original 2A10 heavy chain sequence.

In addition, one of skill in the art does not need to rely on previously identified antibodies to practice the instant invention, but instead can prepare an antibody to a target of interest for use in the present invention using standard antibody production techniques. Several of such techniques are described in detail below and others are well known in the art, for example those described in Lonberg, N. et al. (1994) Nature 368(6474): 856 859; Fishwild, D. et al. (1996) Nature Biotechnology 14: 845-851; and PCT Publication WO 98/24884 and WO 01/14424.

In a preferred embodiment, the antibodies of the instant invention are Affibodies. Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, Nat Biotechnol 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren Pa., Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

In a preferred embodiment, the antibodies of the instant application are Domain Antibodies (dAbs). dAbs are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; U.S. Application No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

In a preferred embodiment the antibodies of the instant invention are Nanobodies. Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanised without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognising uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), moulds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells.

In a preferred embodiment the antibodies of the instant invention are UniBodies. UniBody is a new proprietary antibody technology that creates a stable, smaller antibody format with an anticipated longer therapeutic window than current small antibody formats. IgG4 antibodies are considered inert and thus do not interact with the immune system. Genmab modified fully human IgG4 antibodies by eliminating the hinge region of the antibody. Unlike the full size IgG4 antibody, the half molecule fragment is very stable and is termed a UniBody. Halving the IgG4 molecule left only one area on the UniBody that can bind to disease targets and the UniBody therefore binds univalently to only one site on target cells. This univalent binding does not stimulate cancer cells to grow like bivalent antibodies might and opens the door for treatment of some types of cancer which ordinary antibodies cannot treat.

The UniBody is about half the size of a regular IgG4 antibody. This small size can be a great benefit when treating some forms of cancer, allowing for better distribution of the molecule over larger solid tumors and potentially increasing efficacy.

Fabs typically do not have a very long half-life. UniBodies, however, were cleared at a similar rate to whole IgG4 antibodies and were able to bind as well as whole antibodies and antibody fragments in pre-clinical studies. Other antibodies primarily work by killing the targeted cells whereas UniBodies only inhibit or silence the cells.

Further details of Unibodies may be obtained by reference to patent WO2007/059782, which is herein incorporated by reference in its entirety.

Conjugates

In another aspect, there is provided an antibody-partner molecule conjugate, wherein a partner molecule is conjugated to an antibody having a C-terminal cysteine-bearing extension according to this invention by a chemical linker (sometimes referred to herein simply as "linker"). The partner molecule can be a therapeutic agent or a marker. The therapeutic agent can be, for example, a cytotoxin, a non-cytotoxic drug (e.g., an immunosuppressant), a radioactive agent, another antibody, or an enzyme. Preferably, the partner molecule is a cytotoxin. The marker can be any label that generates a detectable signal, such as a radiolabel, a fluorescent label, or an enzyme that catalyzes a detectable modification to a substrate. The antibody serves a targeting function: by binding to a target tissue or cell where its antigen is found, the antibody steers the conjugate to the target tissue or cell. There, the linker is cleaved, releasing the partner molecule to perform its desired biological function. In some instances, the conjugate is internalized within a target cell and the cleavage occurs therewithin.

Linkers

In some embodiments, the linker is a peptidyl linker, depicted herein as $(L^4)_p$-F-$(L^1)_m$. Other linkers include hydrazine and disulfide linkers, depicted herein as $(L^4)_p$-H-$(L^1)_m$ and $(L^4)_p$-J-$(L^1)_m$, respectively. F, H, and J are peptidyl, hydrazine, and disulfide moieties, respectively, that are cleavable to release the partner molecule from the antibody, while $L^1$ and $L^4$ are linker groups. F, H, J, $L^1$, and $L^4$ are more fully defined hereinbelow, along with the subscripts p and m. The preparation and use of these and other linkers is described in WO 2005/112919, the disclosure of which is incorporated herein by reference.

The use of peptidyl and other linkers in antibody-partner conjugates is described in U.S. Provisional Patent Application Ser. Nos. 60/295,196; 60/295,259; 60/295,342; 60/304,908; 60/572,667; 60/661,174; 60/669,871; 60/720,499; 60/730,804; and 60/735,657; published U.S. Patent Applications 2006/0004081, 2006/0024317, and 2006/0247295; U.S. Pat. Nos. 6,989,452, 7,087,800; and 7,129,261; PCT Patent Application No. PCT/US2007/089100; and published PCT applications Nos. 2007/038658, 2007/059404, and 2007/089100, all of which are incorporated herein by reference.

Additional linkers are described in U.S. Pat. No. 6,214,345 (Bristol-Myers Squibb), U.S. Pat. Appl. 2003/0096743 and U.S. Pat. Appl. 2003/0130189 (both to Seattle Genetics), de Groot et al., J. Med. Chem. 42, 5277 (1999); de Groot et al. J. Org. Chem. 43, 3093 (2000); de Groot et al., J. Med. Chem. 66, 8815, (2001); WO 02/083180 (Syntarga); Carl et al., J. Med. Chem. Lett. 24, 479, (1981); Dubowchik et al., Bioorg & Med. Chem. Lett. 8, 3347 (1998), the disclosures of which are incorporated herein by reference.

In addition to connecting the antibody and the partner molecule, a linker can impart stability to the partner molecule, reduce its in vivo toxicity, or otherwise favorably affect its pharmacokinetics, bioavailability and/or pharmacodynamics. It is generally preferred that the linker is cleaved, releasing the partner molecule, once the conjugate is delivered to its site of action. Also preferably, the linkers are traceless, such that once removed from the partner molecule (such as during activation), no trace of the linker's presence remains.

In another embodiment, the linkers are characterized by their ability to be cleaved at a site in or near a target cell such as at the site of therapeutic action or marker activity of the partner molecule. Such cleavage can be enzymatic in nature. This feature aids in reducing systemic activation of the partner molecule, reducing toxicity and systemic side effects. Preferred cleavable groups for enzymatic cleavage include peptide bonds, ester linkages, and disulfide linkages, such as the aforementioned F, H, and J moieties. In other embodiments, the linkers are sensitive to pH and are cleaved through changes in pH.

An important aspect is the ability to control the speed with which the linkers cleave. Often a linker that cleaves quickly is desired. In some embodiments, however, a linker that cleaves more slowly may be preferred. For example, in a sustained release formulation or in a formulation with both a quick release and a slow release component, it may be useful to provide a linker which cleaves more slowly. The aforecited WO 2005/112919 discloses hydrazine linkers that can be designed to cleave at a range of speeds, from very fast to very slow.

The linkers can also serve to stabilize the partner molecule against degradation while the conjugate is in circulation, that is, before it reaches the target tissue or cell. This feature provides a significant benefit since such stabilization results in a prolongation of the circulation half-life of the partner molecule. The linker also serves to attenuate the activity of the partner molecule so that the conjugate is relatively benign while in circulation but the partner molecule has the desired effect—for example is cytotoxic—after activation at the desired site of action. For therapeutic agent conjugates, this feature of the linker serves to improve the therapeutic index of the agent.

In addition to the cleavable peptide, hydrazine, or disulfide groups F, H, or J, respectively, one or more linker groups $L^1$ are optionally introduced between the partner molecule and F, H, or J, as the case may be. These linker groups $L^1$ may also be described as spacer groups and contain at least two functional groups. Depending on the value of the subscript m (i.e., the number of $L^1$ groups present) and the location of a particular group $L^1$, a chemical functionality of a group $L^1$ can bond to a chemical functionality of the partner molecule, of F, H or J, as the case may be, or of another linker group $L^1$ (if more than one $L^1$ is present). Examples of suitable chemical functionalities for spacer groups $L^1$ include hydroxy, mercapto, carbonyl, carboxy, amino, ketone, aldehyde, and mercapto groups.

The linkers $L^1$ can be a substituted or unsubstituted alkyl, substituted or unsubstituted aryl, substituted or unsubstituted heteroaryl or substituted or unsubstituted heteroalkyl group. In one embodiment, the alkyl or aryl groups may comprise between 1 and 20 carbon atoms. They may also comprise a polyethylene glycol moiety.

Exemplary groups $L^1$ include, for example, 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

One function of the groups $L^1$ is to provide spatial separation between F, H or J, as the case may be, and the partner molecule, lest the latter interfere (e.g., via steric or electronic effects) with the cleavage chemistry at F, H, or J. The groups $L^1$ also can serve to introduce additional molecular mass and chemical functionality into conjugate. Generally, the additional mass and functionality will affect the serum half-life and other properties of the conjugate. Thus, through careful selection of spacer groups, conjugates with a range of serum half-lives can be produced. Optionally, one or more linkers $L^1$ can be a self-immolative group, as described hereinbelow.

The subscript m is an integer selected from 0, 1, 2, 3, 4, 5, and 6. When multiple $L^1$ groups are present, they can be the same or different.

$L^4$ is a linker moiety that provides spatial separation between F, H, or J, as the case may be, and the antibody, lest F, H, or J interfere with the antigen binding by the antibody or the antibody interfere with the cleavage chemistry at F, H, or J. Preferably, $L^4$ imparts increased solubility or decreased aggregation properties to conjugates utilizing a linker that contains the moiety or modifies the hydrolysis rate of the conjugate. As in the case of $L^1$, $L^4$ optionally is a self immolative group. In one embodiment, the $L^4$ moiety is substituted alkyl, unsubstituted alkyl, substituted aryl, unsubstituted aryl, substituted heteroalkyl, or unsubstituted heteroalkyl, any of which may be straight, branched, or cyclic. The substitutions can be, for example, a lower ($C_1$-$C_6$) alkyl, alkoxy, alkylthio, alkylamino, or dialkylamino. In certain embodiments, $L^4$ comprises a non-cyclic moiety. In another embodiment, $L^4$ comprises a positively or negatively charged amino acid polymer, such as polylysine or polyarginine. $L^4$ can comprise a polymer such as a polyethylene glycol moiety. Additionally the $L^4$ linker can comprise, for example, both a polymer component and a small molecule moiety.

In a preferred embodiment, $L^4$ comprises a polyethylene glycol (PEG) moiety. The PEG portion of $L^4$ may be between 1 and 50 units long. Preferably, the PEG will have 1-12 repeat units, more preferably 3-12 repeat units, more preferably 2-6 repeat units, or even more preferably 3-5 repeat units and most preferably 4 repeat units. $L^4$ may consist solely of the PEG moiety, or it may also contain an additional substituted or unsubstituted alkyl or heteroalkyl. It is useful to combine PEG as part of the $L^4$ moiety to enhance the water solubility of the complex. Additionally, the PEG moiety reduces the degree of aggregation that may occur during the conjugation of the drug to the antibody.

The subscript p is 0 or 1; that is, the presence of $L^4$ is optional. Where present, $L^4$ has at least two functional groups, with one functional group binding to a chemical functionality in F, H, or J, as the case may be, and the other functional group binding to the antibody. Examples of suitable chemical functionalities of groups $L^4$ include hydroxy, mercapto, carbonyl, carboxy, amino, ketone, aldehyde, and mercapto groups. In the present instance of antibodies having a cysteine-bearing C-terminal H chain extension, the functional group for binding to the antibody should be one reactive with sulfhydryl groups. Examples of suitable ones include another sulfhydryl group (for formation of a disulfide) or, preferably, a maleimide group (for addition of the antibody sulfhydryl group across the maleimide double bond).

In some embodiments, $L^4$ comprises

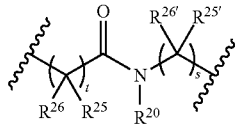

directly attached to the N-terminus of $(AA^1)_c$. $R^{20}$ is a member selected from H, substituted or unsubstituted alkyl, substituted or unsubstituted heteroalkyl, and acyl. Each $R^{25}$, $R^{25'}$, $R^{26}$, and $R^{26'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; and s and t are independently integers from 1 to 6. Preferably, $R^{20}$, $R^{25}$, $R^{25'}$, $R^{26}$ and $R^{26'}$ are hydrophobic. In some embodiments, $R^{20}$ is H or alkyl (preferably, unsubstituted lower alkyl). In some embodiments, $R^{25}$, $R^{25'}$, $R^{26}$ and $R^{26'}$ are independently H or alkyl (preferably, unsubstituted $C^1$ to $C^4$ alkyl). In some embodiments, $R^{25}$, $R^{25'}$, $R^{26}$ and $R^{26'}$ are all H. In some embodiments, t is 1 and s is 1 or 2.

Peptide Linkers (F)

As discussed above, the peptidyl linkers of the invention can be represented by the general formula: $(L^4)_p$-F-$(L^1)_m$, wherein F represents the portion comprising the peptidyl moiety. In one embodiment, the F portion comprises an optional additional self-immolative linker $L^2$ and a carbonyl group, corresponding to a conjugate of formula (a):

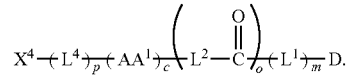

In this embodiment, $L^1$, $L^4$, p, and m are as defined above. $X^4$ is an antibody and D is a partner molecule. The subscript o is 0 or 1 and $L^2$, if present, represents a self-immolative linker. The subscript o is 0 or 1. $AA^1$ represents one or more natural amino acids, and/or unnatural α-amino acids; c is an integer from 1 and 20. In some embodiments, c is in the range of 2 to 5 or c is 2 or 3.

In formula (a), $AA^1$ is linked, at its amino terminus, either directly to $L^4$ or, when $L^4$ is absent, directly to $X^4$. In some embodiments, when $L^4$ is present, $L^4$ does not comprise a carboxylic acyl group directly attached to the N-terminus of $(AA^1)_c$.

In another embodiment, the F portion comprises an amino group and an optional spacer group $L^3$ and $L^1$ is absent (i.e., m is 0), corresponding to a conjugate of formula (b):

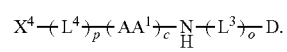

In this embodiment, $X^4$, D, $L^4$, $AA^1$, c, and p are as defined above. The subscript o is 0 or 1. $L^3$, if present, is a spacer group comprising a primary or secondary amine or a carboxyl functional group, and either the amine of $L^3$ forms an amide bond with a pendant carboxyl functional group of D or the carboxyl of $L^3$ forms an amide bond with a pendant amine functional group of D.

Self-Immolative Linkers

A self-immolative linker is a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the peptide moiety and covalently linked at its other end to the chemically reactive site of the drug moiety whose derivatization inhibits pharmacological activity, so as to space and covalently link together the peptide moiety and the drug moiety into a tripartate molecule which is stable and pharmacologically inactive in the absence of the target enzyme, but which is enzymatically cleavable by such target enzyme at the bond covalently linking the spacer moiety and the peptide moiety to thereby effect release of the peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form. See, for example, Carl et al., 3. Med. Chem., 24 (3), 479-480 (1981); Carl et al., WO 81/01145 (1981); Toki et al., J. Org. Chem. 67, 1866-1872 (2002); Boyd et al., WO 2005/112919; and Boyd et al., WO 2007/038658, the disclosures of which are incorporated herein by reference.

One particularly preferred self-immolative spacer may be represented by the formula (c):

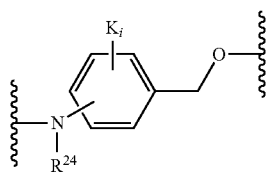

The aromatic ring of the aminobenzyl group may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Each K is independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$, wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl. Exemplary K substituents include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In one preferred embodiment, i is 0.

The ether oxygen atom of the structure shown above is connected to a carbonyl group. The line from the $NR^{24}$ functionality into the aromatic ring indicates that the amine functionality may be bonded to any of the five carbons that both form the ring and are not substituted by the —$CH_2$—O— group. Preferably, the $NR^{24}$ functionality of X is covalently bound to the aromatic ring at the para position relative to the —$CH_2$—O— group. $R^{24}$ is a member selected from the group consisting of H, substituted alkyl, unsubstituted alkyl, substituted heteroalkyl, and unsubstituted heteroalkyl. In a specific embodiment, $R^{24}$ is hydrogen.

In one embodiment, the invention provides a peptide linker of formula (a) above, wherein F comprises the structure:

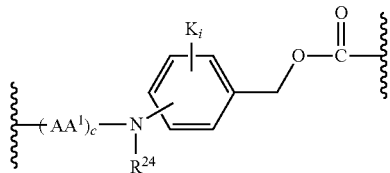

where $R^{24}$, $AA^1$, K, i, and c are as defined above.

In another embodiment, the peptide linker of formula (a) above comprises a —F-$(L^1)_m$- that comprises the structure:

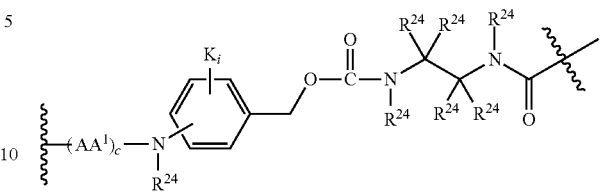

where $R^{24}$, $AA^1$, K, i, and c are as defined above.

In some embodiments, a self-immolative spacer $L^1$ or $L^2$ includes

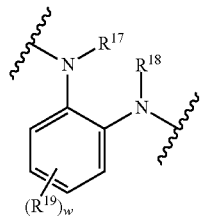

where each $R^{17}$, $R^{18}$, and $R^{19}$ is independently selected from H, substituted or unsubstituted alkyl, substituted or unsubstituted heteroalkyl and substituted or unsubstituted aryl, and w is an integer from 0 to 4. In some embodiments, $R^{17}$ and $R^{18}$ are independently H or alkyl (preferably, unsubstituted $C_1$-$C_4$ alkyl). Preferably, $R^{17}$ and $R^{18}$ are C1-4 alkyl, such as methyl or ethyl. In some embodiments, w is 0. It has been found experimentally that this particular self-immolative spacer cyclizes relatively quickly.

In some embodiments, $L^1$ or $L^2$ includes

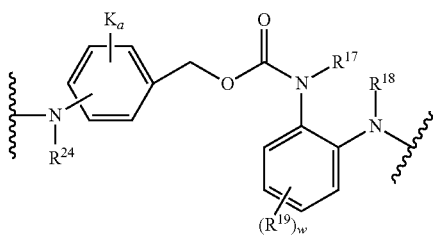

where $R^{17}$, $R^{18}$, $R^{19}$, $R^{24}$, and K are as defined above.

Spacer Groups

The spacer group $L^3$ is characterized in that it comprises a primary or secondary amine or a carboxyl functional group, and either the amine of the $L^3$ group forms an amide bond with a pendant carboxyl functional group of D or the carboxyl of $L^3$ forms an amide bond with a pendant amine functional group of D. $L^3$ can be selected from the group consisting of substituted or unsubstituted alkyl, substituted or unsubstituted heteroalkyl, substituted or unsubstituted aryl, substituted or unsubstituted heteroaryl, or substituted or unsubstituted heterocycloalkyl. In a preferred embodiment, $L^3$ comprises an aromatic group. More preferably, $L^3$ comprises a benzoic acid group, an aniline group or indole group. Non-limiting examples of structures that can serve as an -$L^3$-NH— spacer include the following structures:

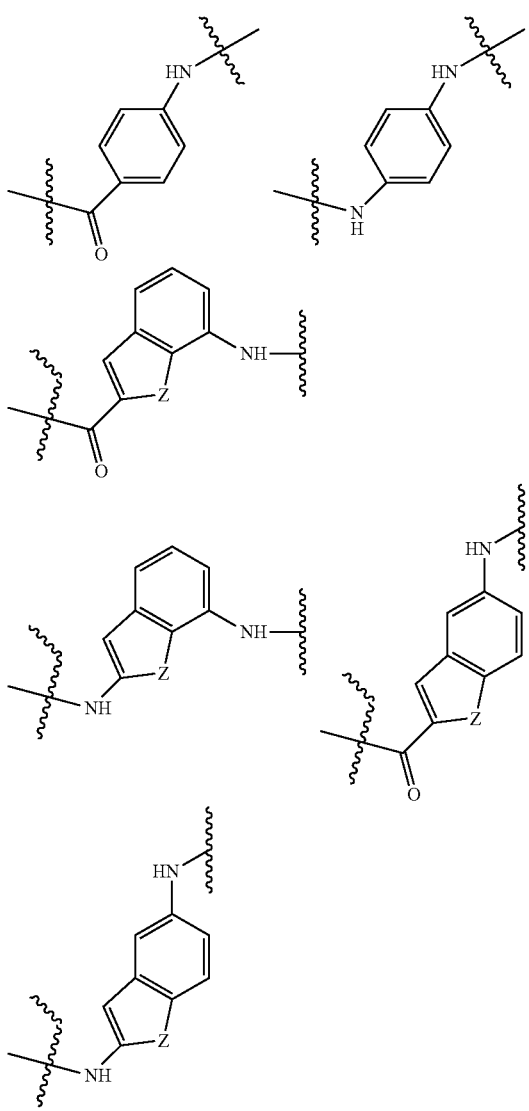

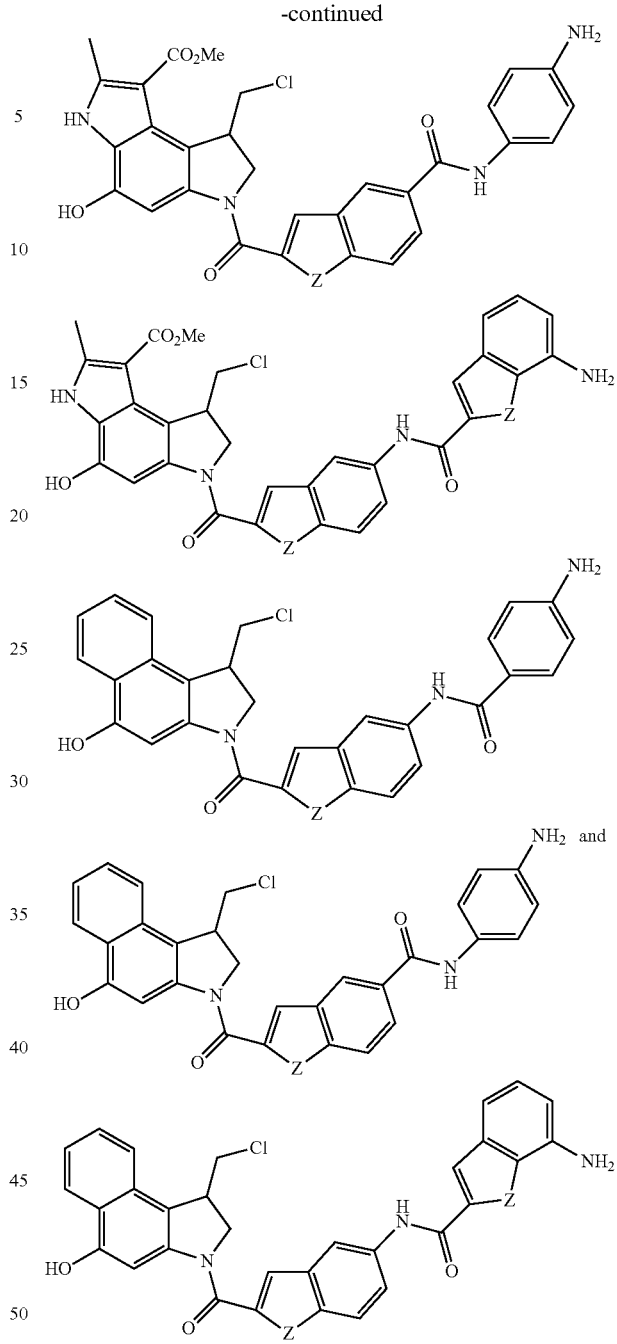

where Z is a member selected from O, S and NR²³, and where R²³ is a member selected from H, substituted or unsubstituted alkyl, substituted or unsubstituted heteroalkyl, and acyl.

Upon cleavage of the linker of the invention containing L³, the L³ moiety remains attached to the drug, D. Accordingly, the L³ moiety is chosen such that its attachment to D does not significantly alter the activity of D. In another embodiment, a portion of the drug D itself functions as the L³ spacer. For example, in one embodiment, the drug, D, is a duocarmycin derivative in which a portion of the drug functions as the L³ spacer. Non-limiting examples of such embodiments include those in which NH₂-(L³)-D has a structure selected from the group consisting of:

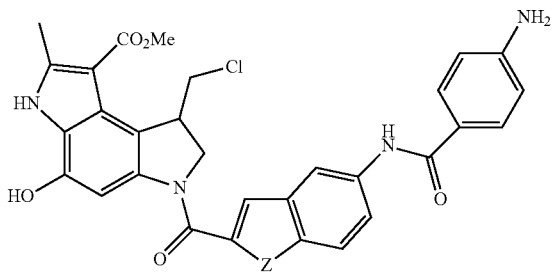

where Z is O, S or NR²³, where R²³ is H, substituted or unsubstituted alkyl, substituted or unsubstituted heteroalkyl, or acyl; and the NH₂ group on each structure reacts with $(AA^1)_c$ to form $-(AA^1)_c$—NH—.

Peptide Sequence $(AA^1)_c$

The group AA¹ represents a single amino acid or a plurality of amino acids that are joined together by amide bonds. The amino acids may be natural amino acids and/or unnatural α-amino acids. They may be in the L or the D configuration. In one embodiment, at least three different amino acids are used. In another embodiment, only two amino acids are used.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, citrulline, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

The peptide sequence $(AA^1)_c$ is functionally the amidification residue of a single amino acid (when c=1) or a plurality of amino acids joined together by amide bonds. The peptide sequence $(AA^1)_c$ preferably is selected for enzyme-catalyzed cleavage by an enzyme in a location of interest in a biological system. For example, for conjugates that are targeted to but not internalized by a cell, a peptide is chosen that is cleaved by a protease that in in the extracellular matrix, e.g., a protease released by nearby dying cells or a tumor-associated protease, such that the peptide is cleaved extracellularly. For conjugates that are designed for internalization by a cell, the sequence $(AA^1)_c$ preferably is selected for cleavage by an endosomal or lysosomal protease. The number of amino acids within the peptide can range from 1 to 20; but more preferably there will be 1-8 amino acids, 1-6 amino acids or 1, 2, 3 or 4 amino acids comprising $(AA^1)_c$. Peptide sequences that are susceptible to cleavage by specific enzymes or classes of enzymes are well known in the art.

Preferably, $(AA^1)_c$ contains an amino acid sequence ("cleavage recognition sequence") that is a cleavage site by the protease. Many protease cleavage sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al., in Amyloid Protein Precursor in Development, Aging, and Alzheimer's Disease, ed. Masters et al. pp. 190-198 (1994).

In a preferred embodiment, the peptide sequence $(AA^1)_c$ is chosen based on its ability to be cleaved by a lysosomal proteases, non-limiting examples of which include cathepsins B, C, D, H, L and S. Preferably, the peptide sequence $(AA^1)_c$ is capable of being cleaved by cathepsin B in vitro.

In another embodiment, the peptide sequence $(AA^1)_c$ is chosen based on its ability to be cleaved by a tumor-associated protease, such as a protease that is found extracellularly in the vicinity of tumor cells, examples of which include thimet oligopeptidase (TOP) and CD10. In other embodiments, the sequence $(AA^1)_c$ is designed for selective cleavage by urokinase or tryptase.

Suitable, but non-limiting, examples of peptide sequences suitable for use in the conjugates of the invention include Val-Cit, Cit-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO:10), β-Ala-Leu-Ala-Leu (SEQ ID NO:11) and Gly-Phe-Leu-Gly (SEQ. ID NO: 9) Val-Ala, Leu-Leu-Gly-Leu (SEQ ID NO:12), Leu-Asn-Ala, and Lys-Leu-Val. Preferred peptides sequences are Val-Cit and Val-Lys.

In another embodiment, the amino acid located the closest to the drug moiety is selected from the group consisting of: Ala, Asn, Asp, Cit, Cys, Gln, Glu, Gly, Ile, Leu, Lys, Met, Phe, Pro, Ser, Thr, Trp, Tyr, and Val. In yet another embodiment, the amino acid located the closest to the drug moiety is selected from the group consisting of: Ala, Asn, Asp, Cys, Gln, Glu, Gly, Ile, Leu, Met, Phe, Pro, Ser, Thr, Trp, Tyr, and Val.

One of skill in the art can readily evaluate an array of peptide sequences to determine their utility in the present invention without resort to undue experimentation. See for example, Zimmerman, M., et al., (1977) *Analytical Biochemistry* 78:47-51; Lee, D., et al., (1999) *Bioorganic and Medicinal Chemistry Letters* 9:1667-72; and Rano, T. A., et al., (1997) *Chemistry and Biology* 4:149-55.

A conjugate of this invention may optionally contain two or more linkers. These linkers may be the same or different. For example, a peptidyl linker may be used to connect the drug to the ligand and a second peptidyl linker may attach a diagnostic agent to the complex. Other uses for additional linkers include linking analytical agents, biomolecules, targeting agents, and detectable labels to the antibody-partner complex.

Hydrazine Linkers (H)

In another embodiment, the conjugate of the invention comprises a hydrazine self-immolative linker, wherein the conjugate has the structure:

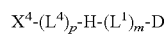

wherein D, L$^1$, L$^4$, p, m, and X$^4$ are as defined above and described further herein, and H is a linker comprising the structure:

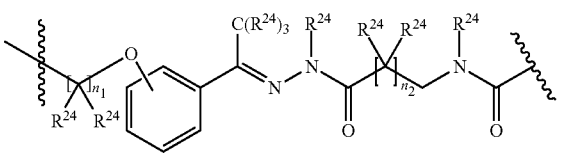

wherein n$_1$ is an integer from 1-10; n$_2$ is 0, 1, or 2; each R$^{24}$ is a member independently selected from the group consisting of H, substituted alkyl, unsubstituted alkyl, substituted heteroalkyl, and unsubstituted heteroalkyl; and I is either a bond (i.e., the bond between the carbon of the backbone and the adjacent nitrogen) or:

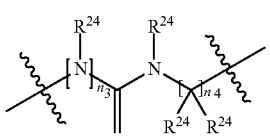

wherein $n_3$ is 0 or 1, with the proviso that when $n_3$ is 0, $n_2$ is not 0; and $n_4$ is 1, 2, or 3.

In one embodiment, the substitution on the phenyl ring is a para substitution. In preferred embodiments, $n_1$ is 2, 3, or 4 or $n_1$ is 3. In preferred embodiments, $n_2$ is 1. In preferred embodiments, I is a bond (i.e., the bond between the carbon of the backbone and the adjacent nitrogen). In one aspect, the hydrazine linker, H, can form a 6-membered self immolative linker upon cleavage, for example, when $n_3$ is 0 and $n_4$ is 2. In another aspect, the hydrazine linker, H, can form two 5-membered self immolative linkers upon cleavage. In yet other aspects, H forms a 5-membered self immolative linker, H forms a 7-membered self immolative linker, or H forms a 5-membered self immolative linker and a 6-membered self immolative linker, upon cleavage. The rate of cleavage is affected by the size of the ring formed upon cleavage. Thus, depending upon the rate of cleavage desired, an appropriate size ring to be formed upon cleavage can be selected.

Another hydrazine structure, H, has the formula:

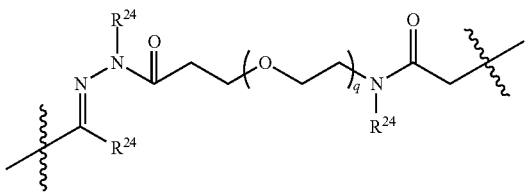

where q is 0, 1, 2, 3, 4, 5, or 6; and each $R^{24}$ is a member independently selected from the group consisting of H, substituted alkyl, unsubstituted alkyl, substituted heteroalkyl, and unsubstituted heteroalkyl. This hydrazine structure can also form five-, six-, or seven-membered rings and additional components can be added to form multiple rings.

The preparation, cleavage chemistry and cyclization kinetics of the various hydrazine linkers is disclosed in WO 2005/112919, the disclosure of which is incorporated herein by reference.

Disulfide Linkers (J)

In yet another embodiment, the linker comprises an enzymatically cleavable disulfide group. In one embodiment, the invention provides a cytotoxic antibody-partner compound having a structure according to Formula (d):

$$X^4\text{-}[\text{-}(L^4)_p\text{-}J\text{-}(L^1)_m\text{-}]\text{-}D$$

wherein D, $L^1$, $L^4$, p, m, and $X^4$ are as defined above and described further herein, and J is a disulfide linker comprising a group having the structure:

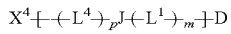
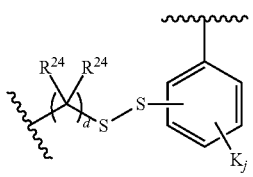

wherein each $R^{24}$ is a member independently selected from the group consisting of H, substituted alkyl, unsubstituted alkyl, substituted heteroalkyl, and unsubstituted heteroalkyl; each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$ wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl; i is an integer of 0, 1, 2, 3, or 4; and d is an integer of 0, 1, 2, 3, 4, 5, or 6.

The aromatic ring of the disulfides linker may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Exemplary K substituents independently include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In a specific embodiment, i is 0.

In a preferred embodiment, the linker comprises an enzymatically cleavable disulfide group of the following formula:

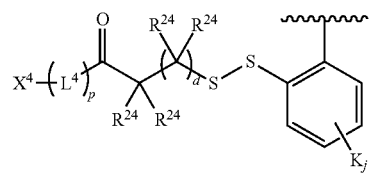

wherein $L^4$, $X^4$, p, and $R^{24}$ are as described above, and d is 0, 1, 2, 3, 4, 5, or 6. In a particular embodiment, d is 1 or 2.

A more specific disulfide linker is shown in the formula below:

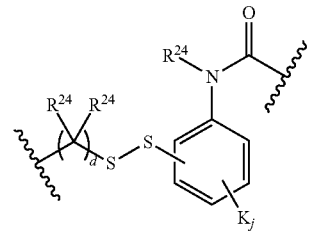

Preferably, d is 1 or 2 and each K is H.

Another disulfide linker is shown in the formula below:

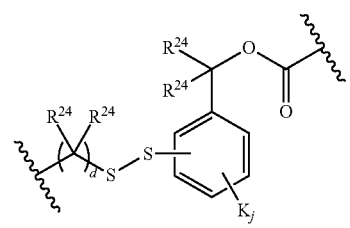

Preferably, d is 1 or 2 and each K is H.

In various embodiments, the disulfides are ortho to the amine. In another specific embodiment, a is 0. In preferred embodiments, $R^{24}$ is independently selected from H and $CH_3$.

The preparation and chemistry of disulfide linkers such as those described above is disclosed in WO 2005/112919, the disclosure of which is incorporated herein by reference.

Alternatively, the group $L^4$ in formula (d) is absent and a disulfide bond is formed directly with the cysteine sulfhydryl of the C-terminal heavy chain extension.

For further discussion of types of cytotoxins, linkers and other methods for conjugating therapeutic agents to antibodies, see also U.S. Pat. No. 7,087,600; U.S. Pat. No. 6,989,452; U.S. Pat. No. 7,129,261; U.S. Patent Publication No. 2006/0004081; U.S. Patent Publication No. 2006/0247295; WO 02/096910; WO 2007/051081; WO 2005/112919; WO 2007/059404; PCT application no. PCT/US2007/089100; PCT application no. PCT/US2008/054362; Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264, each of which is hereby incorporated by reference in its entirety.

Cytotoxins as Partner Molecules

In one aspect, the present invention features an antibody conjugated to a partner molecule, such as a cytotoxin, a drug (e.g., an immunosuppressant) or a radiotoxin. Such conjugates are also referred to as "immunotoxins." A cytotoxin or cytotoxic agent includes any agent that is detrimental to (e.g., kills) cells.

Examples of partner molecules of the present invention include TAXOL™ paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Examples of partner molecules also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, tubulysin, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of partner molecules that can be conjugated to an antibody of the invention include calicheamicins, maytansines and auristatins, and derivatives thereof. A calicheamicin antibody conjugate is commercially available (MYLOTARG® gemtuzumab ozogamicin; American Home Products).

Preferred examples of partner molecule are analogs and derivatives of CC-1065 and the structurally related duocarmycins. Despite its potent and broad antitumor activity, CC-1065 cannot be used in humans because it causes delayed death in experimental animals, prompting a search for analogs or derivatives with a better therapeutic index.

Many analogues and derivatives of CC-1065 and the duocarmycins are known in the art. The research into the structure, synthesis and properties of many of the compounds has been reviewed. See, for example, Boger et al., Angew. Chem. Int. Ed. Engl. 35: 1438 (1996); and Boger et al., Chem. Rev. 97: 787 (1997). Other disclosures relating to CC-1065 analogs or derivatives include: U.S. Pat. No. 5,101,038; U.S. Pat. No. 5,641,780; U.S. Pat. No. 5,187,186; U.S. Pat. No. 5,070,092; U.S. Pat. No. 5,703,080; U.S. Pat. No. 5,070,092; U.S. Pat. No. 5,641,780; U.S. Pat. No. 5,101,038; U.S. Pat. No. 5,084,468; U.S. Pat. No. 5,739,350; U.S. Pat. No. 4,978,757, U.S. Pat. No. 5,332,837 and U.S. Pat. No. 4,912,227; WO 96/10405; and EP 0,537,575 A1

In a particularly preferred aspect, the partner molecule is a CC-1065/duocarmycin analog having a structure according to the following formula (e):

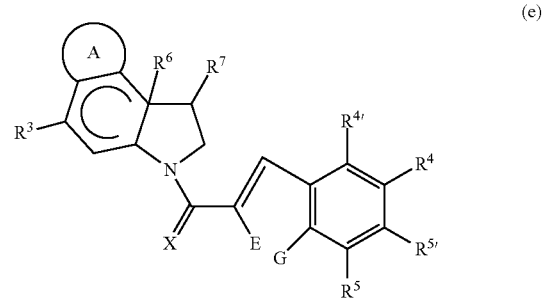

(e)

in which ring system A is a member selected from substituted or unsubstituted aryl substituted or unsubstituted heteroaryl and substituted or unsubstituted heterocycloalkyl groups. Exemplary ring systems A include phenyl and pyrrole.

The symbols E and G are independently selected from H, substituted or unsubstituted alkyl, substituted or unsubstituted heteroalkyl, a heteroatom, a single bond or E and G are optionally joined to form a ring system selected from substituted or unsubstituted aryl, substituted or unsubstituted heteroaryl and substituted or unsubstituted heterocycloalkyl.

The symbol X represents a member selected from O, S and $NR^{23}$. $R^{23}$ is a member selected from H, substituted or unsubstituted alkyl, substituted or unsubstituted heteroalkyl, and acyl.

The symbol $R^3$ represents a member selected from (=O), $SR^{11}$, $NHR^{11}$ and $OR^{11}$, in which $R^{11}$ is H, substituted or unsubstituted alkyl, substituted or unsubstituted heteroalkyl, monophosphates, diphosphates, triphosphates, sulfonates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, where $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms.

$R^4$, $R^{4'}$, $R^5$ and $R^{5'}$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}$=$NR^{16}$, and $O(CH_2)_nN(CH_3)_2$, where n is an integer from 1 to 20, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. One exemplary structure is aniline.

One of $R^3$, $R^4$, $R^{4'}$, $R^5$, and $R^{5'}$ joins the cytotoxin to a linker or enzyme cleavable substrate of the present invention, as described herein, for example to $L^1$ or $L^3$, if present or to F, H, or J.

$R^6$ is a single bond which is either present or absent. When $R^6$ is present, $R^6$ and $R^7$ are joined to form a cyclopropyl ring. $R^7$ is $CH_2$—$X^1$ or —$CH_2$—. When $R^7$ is —$CH_2$— it is a component of the cyclopropane ring. The symbol $X^1$ represents a leaving group such as a halogen, for example Cl, Br or F. The combinations of $R^6$ and $R^7$ are interpreted in a manner that does not violate the principles of chemical valence.

$X^1$ may be any leaving group. Useful leaving groups include, but are not limited to, halogens, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. Particular halogens useful as leaving groups are F, Cl and Br.

The curved line within the six-membered ring indicates that the ring may have one or more degrees of unsaturation, and it may be aromatic. Thus, ring structures such as those set forth below, and related structures, are within the scope of Formula (f):

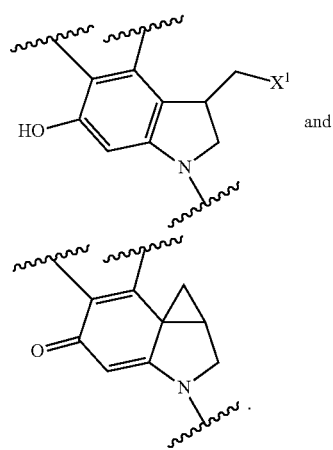

(f)

and

In one embodiment, $R^{11}$ includes a moiety, $X^5$, that does not self-cyclize and links the drug to $L^1$ or $L^3$, if present, or to F, H, or J. The moiety, $X^5$, is preferably cleavable using an enzyme and, when cleaved, provides the active drug. As an example, $R^{11}$ can have the following structure (with the right side coupling to the remainder of the drug):

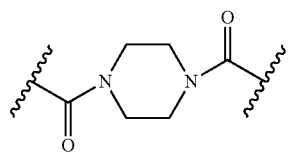 [SMILES: *C(=O)N1CCN(C(*)=O)CC1]

In some embodiments, at least one of $R^4$, $R^{4'}$, $R^5$, and $R^{5'}$ links said drug to $L^1$, if present, or to F, H, J, or $X^2$, and $R^3$ is selected from $SR^{11}$, $NHR^{11}$ and $OR^{11}$. $R^{11}$ is selected from —SO(OH)$_2$, —PO(OH)$_2$, -AA$_n$, —Si(CH$_3$)$_2$C(CH$_3$)$_3$, —C(O)OPhNH(AA)$_m$,

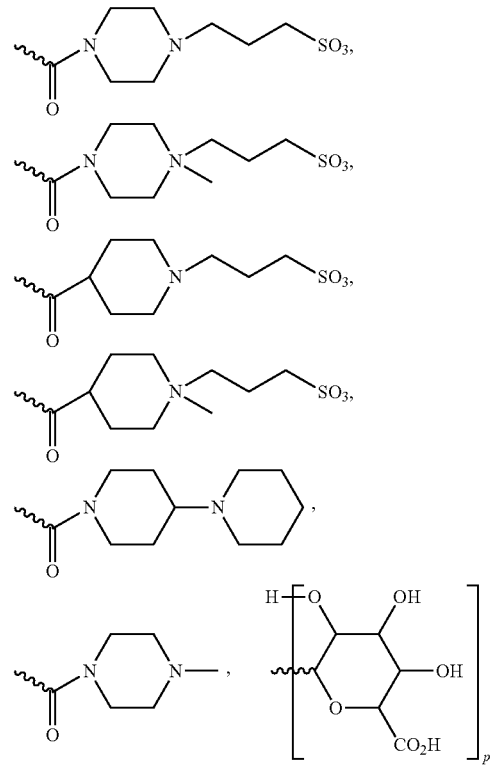

or any other sugar or combination of sugars

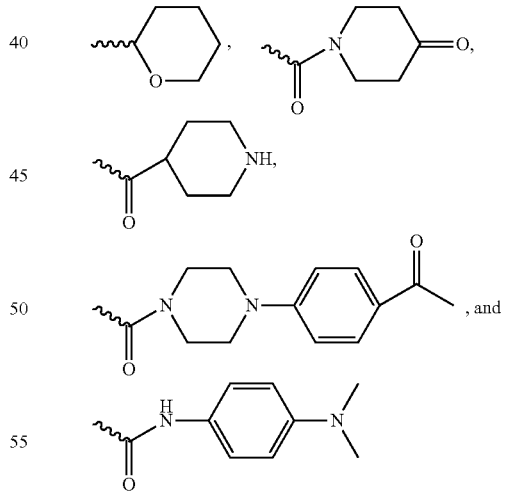

and pharmaceutically acceptable salts thereof, where n is any integer in the range of 1 to 10, m is any integer in the range of 1 to 4, p is any integer in the range of 1 to 6, and AA is any natural or non-natural amino acid. Where the compound of formula (e) is conjugated via $R^4$, $R^{4'}$, $R^5$, or $R^6$, $R^3$ preferably comprises a cleavable blocking group whose presence blocks the cytotoxic activity of the compound but is cleavable under conditions found at the intended site of action by a mechanism different from that for cleavage of the linker conjugating the cytotoxin to the antibody. In this way, if there is adventitious cleavage of the conjugate in the plasma, the blocking group attenuates the cytotoxicity of the released cytotoxin. For instance, if the conjugate has a hydrazone or disulfide linker, the blocking group can be an enzymatically cleavable amide. Or, if the linker is a peptidyl one cleavable by a protease, the blocking group can be an ester or carbamate cleavable by a carboxyesterase.

For example, in a preferred embodiment, D is a cytotoxin having a structure (j):

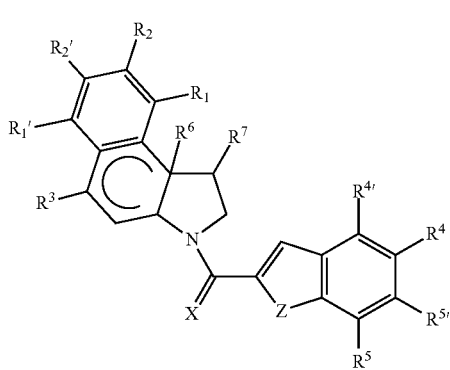

(j)

In this structure, $R^3$, $R^6$, $R^7$, $R^5$, $R^{5'}$ and X are as described above for Formula (e). Z is a member selected from O, S and $NR^{23}$, where $R^{23}$ is a member selected from H, substituted or unsubstituted alkyl, substituted or unsubstituted heteroalkyl, and acyl.

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl.

$R^{1'}$ is H, substituted or unsubstituted lower alkyl, or $C(O)R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl.

$R^2$ is H, or substituted or unsubstituted lower alkyl or unsubstituted heteroalkyl or cyano or alkoxy; and $R^{2'}$ is H, or substituted or unsubstituted lower alkyl or unsubstituted heteroalkyl.

One of $R^3$, $R^4$, $R^{4'}$, $R^5$, or $R^{5'}$ links the cytotoxin to $L^1$ or $L^3$, if present, or to F, H, or.

A further embodiment has the formula:

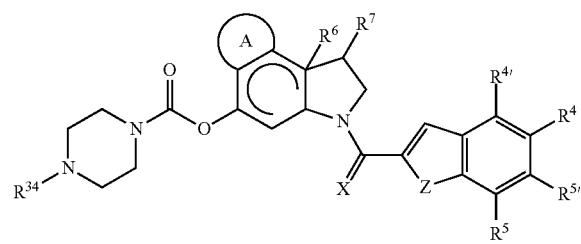

In this structure, A, $R^6$, $R^7$, X, $R^4$, $R^{4'}$, $R^5$, and $R^{5'}$ are as described above for Formula (e). Z is a member selected from O, S and $NR^{23}$, where $R^{23}$ is a member selected from H, substituted or unsubstituted alkyl, substituted or unsubstituted heteroalkyl, and acyl;

$R^{34}$ is $C(=O)R^{33}$ or $C_1$-$C_6$ alkyl, where $R^{33}$ is selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, where n is an integer from 1 to 20. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

Preferably, A is substituted or unsubstituted phenyl or substituted or unsubstituted pyrrole. Moreover, any selection of substituents described herein for $R^{11}$ is also applicable to $R^{33}$.

Markers as Partner Molecules

Where the partner molecule is a marker, it can be any moiety having or generating a detectable physical or chemical property, thereby indicating its presence in a particular tissue or cell. Markers (sometimes also called reporter groups) have been well developed in the area of immunoassays, biomedical research, and medical diagnosis. A marker may be detected by spectroscopic, photochemical, biochemical, immunochemical, electrical, optical or chemical means. Examples include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The marker is preferably a member selected from the group consisting of radioactive isotopes, fluorescent agents, fluorescent agent precursors, chromophores, enzymes and combinations thereof. Examples of suitable enzymes are horseradish peroxidase, alkaline phosphatase, β-galactosidase, and glucose oxidase. Fluorescent agents include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Markers can be attached by indirect means: a ligand molecule (e.g., biotin) is covalently bound to an antibody. The ligand then binds to another molecule (e.g., streptavidin), which is either inherently detectable or covalently bound to a signal system, such as a detectable enzyme, a fluorescent compound, or a chemiluminescent compound.

Examples of Conjugates

Specific examples of partner molecule-linker combinations suitable for conjugation to an antibody of this invention are shown following:

37
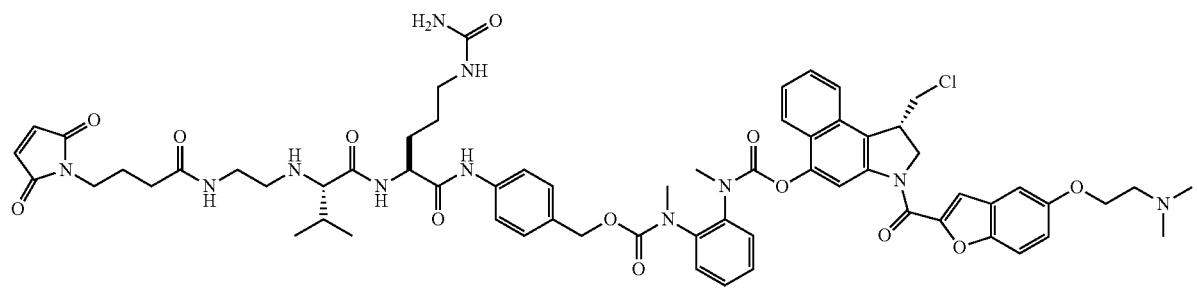
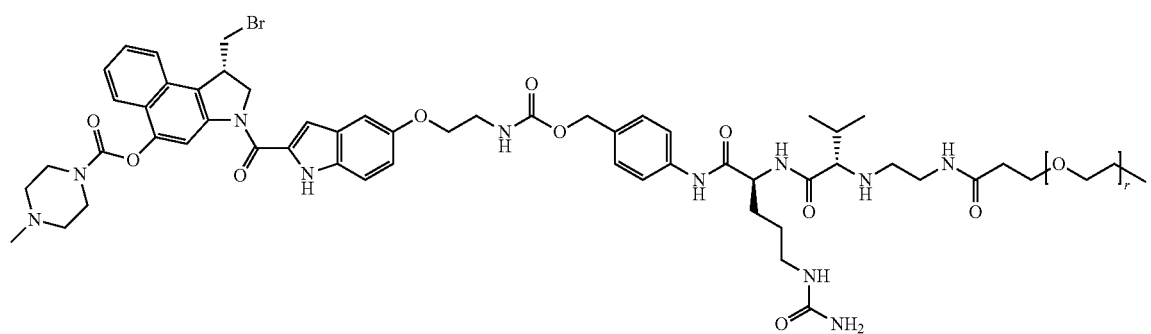
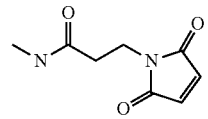
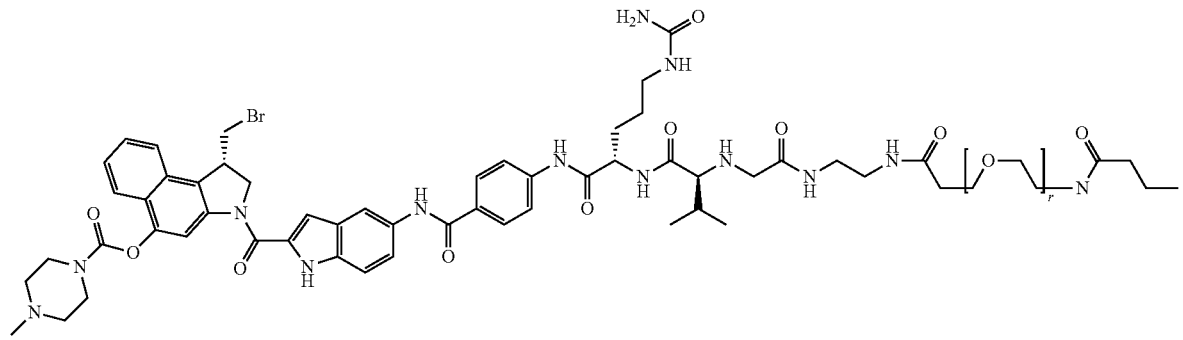
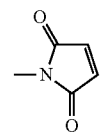
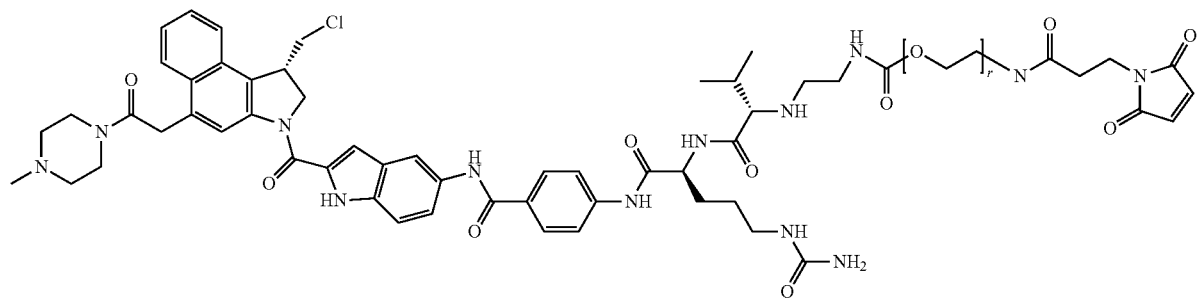

formula (m)
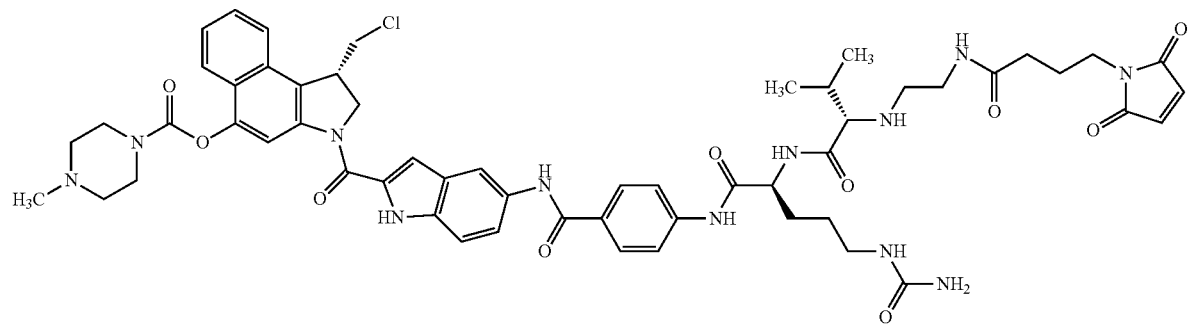
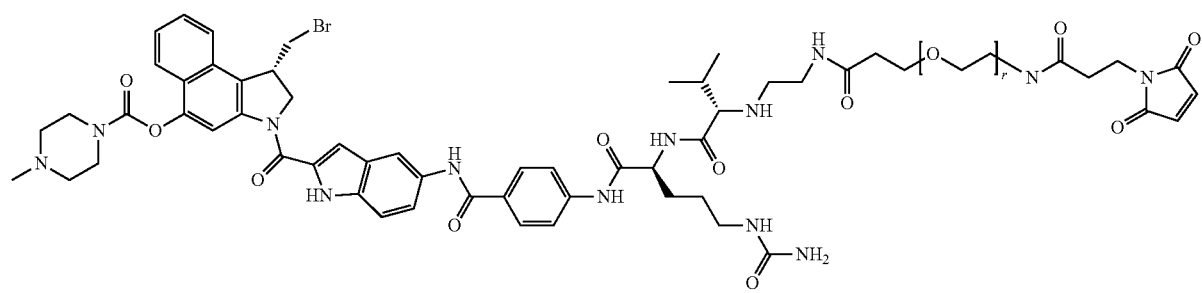
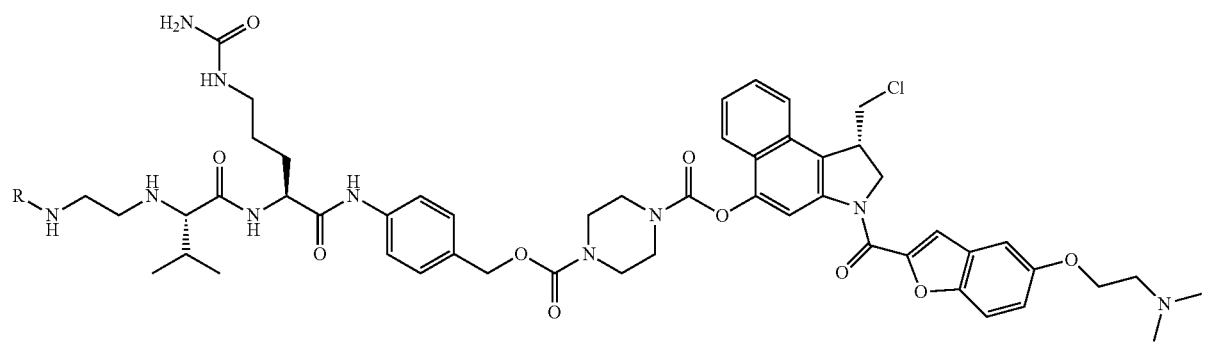
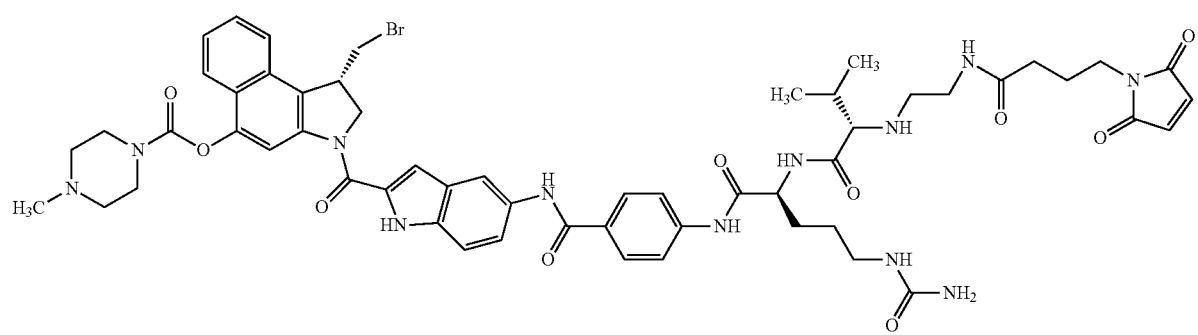

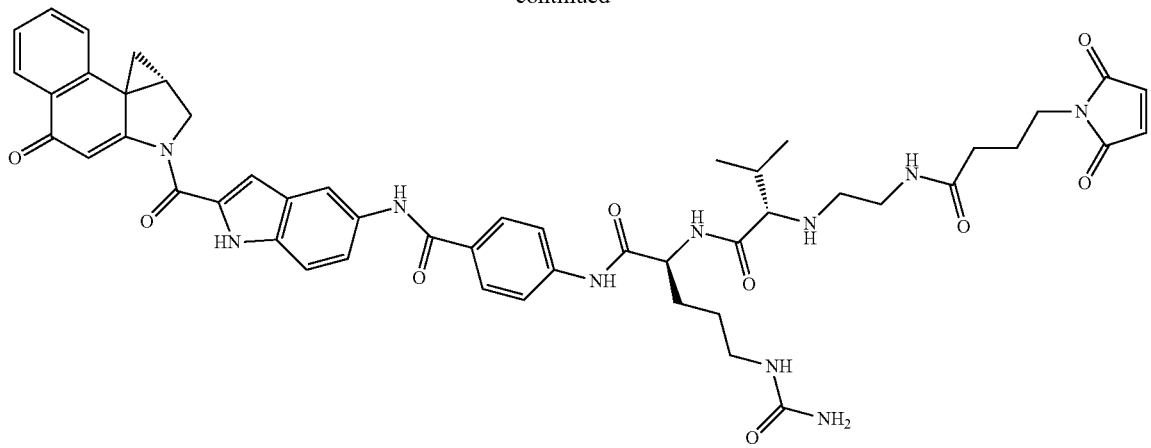
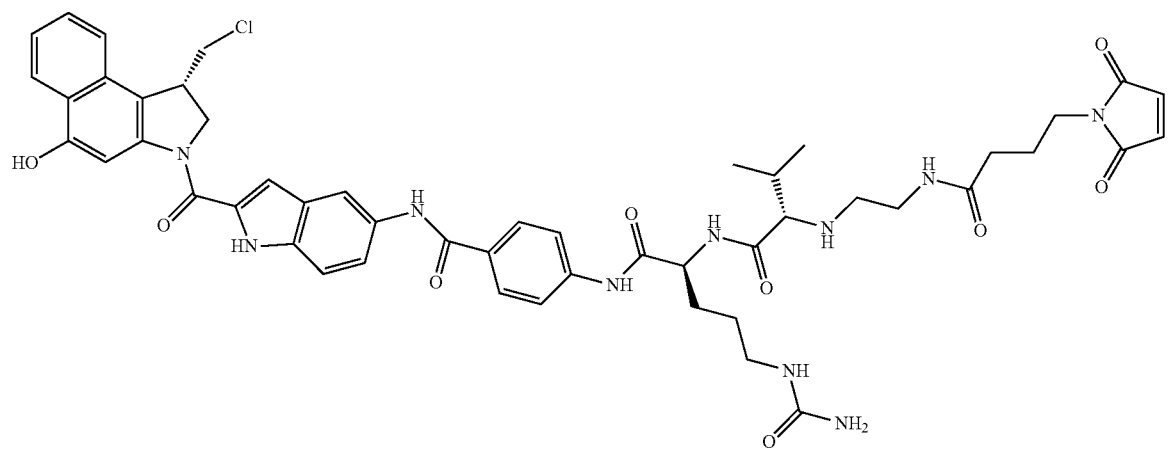
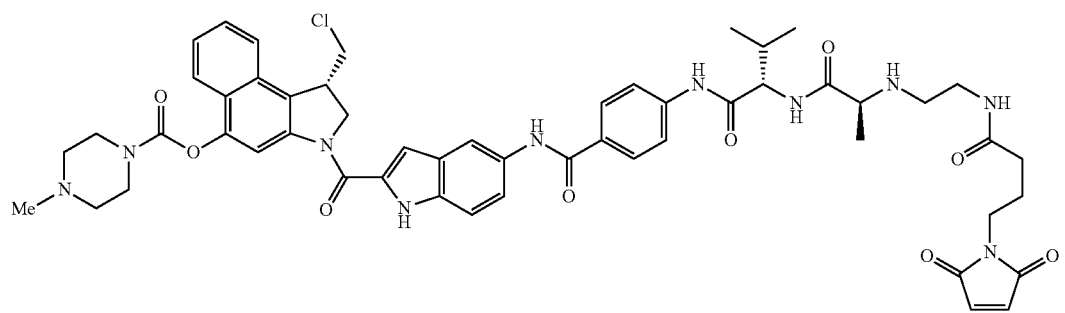
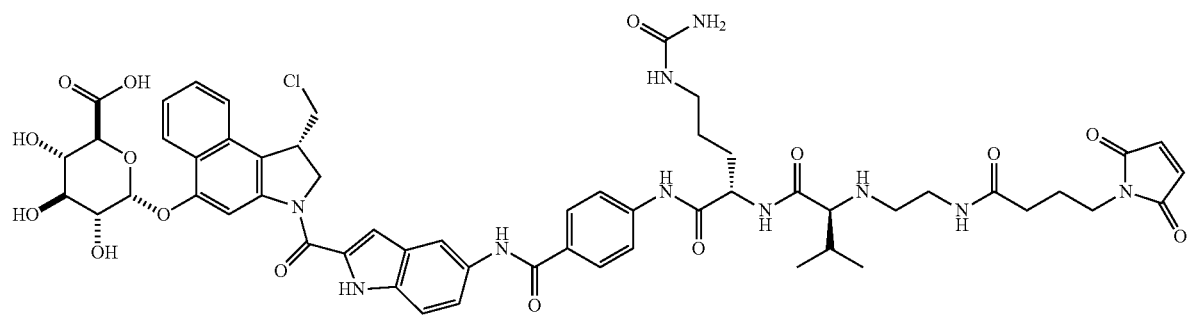

-continued
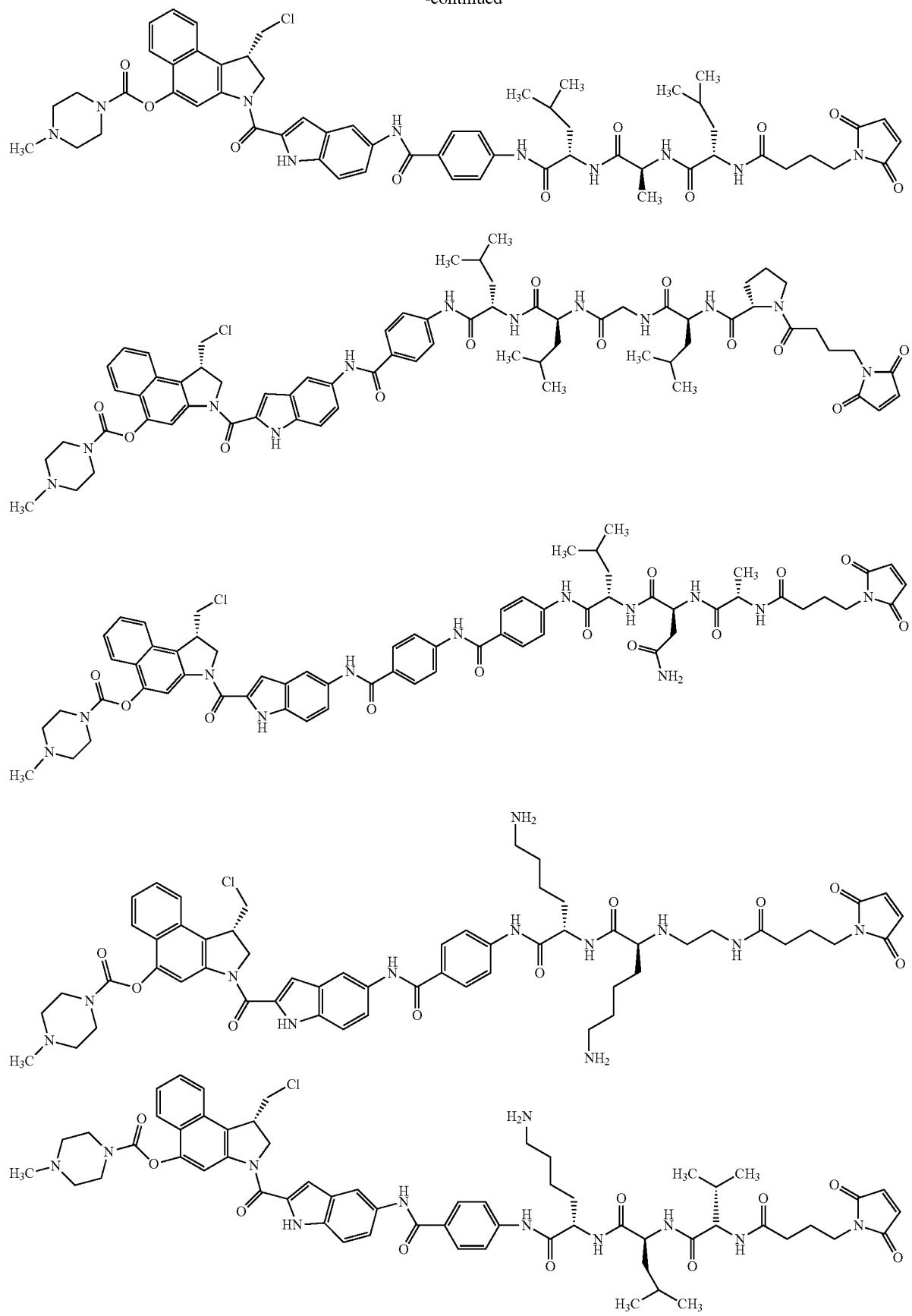

-continued
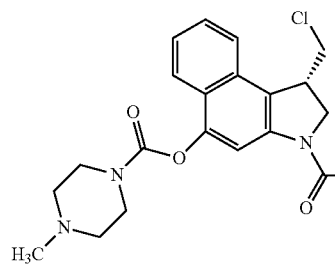
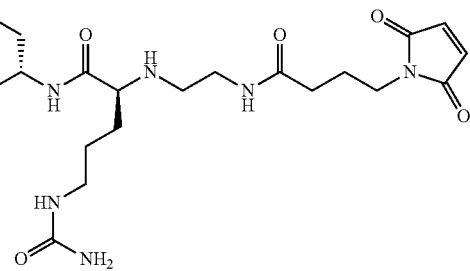
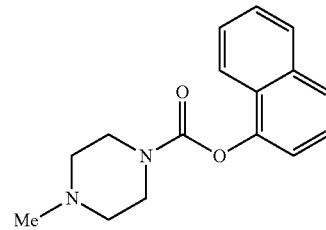
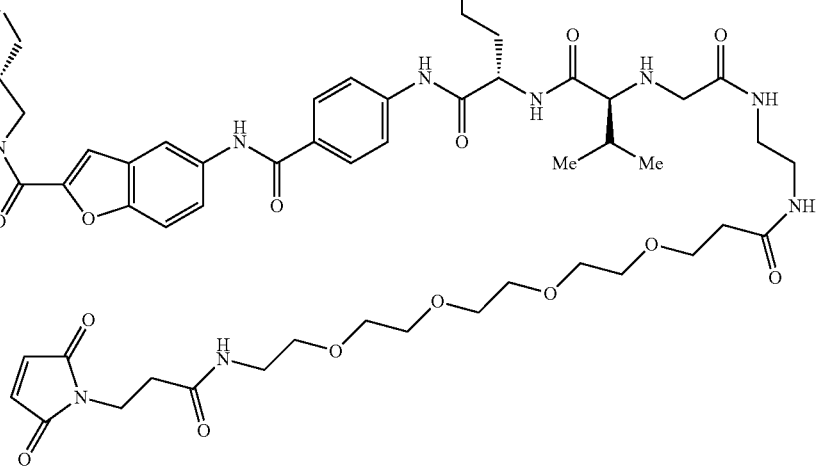
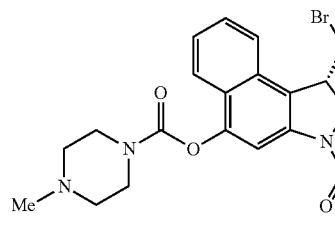
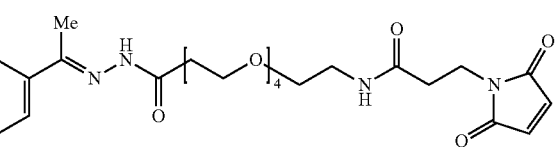
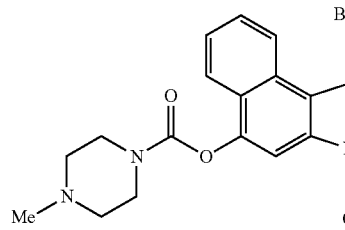
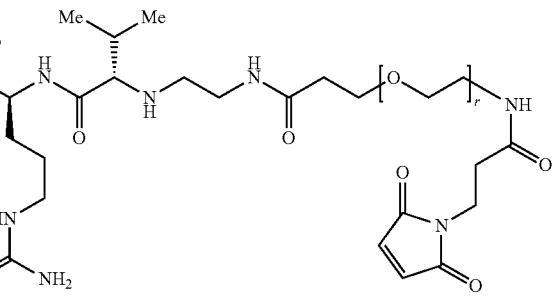

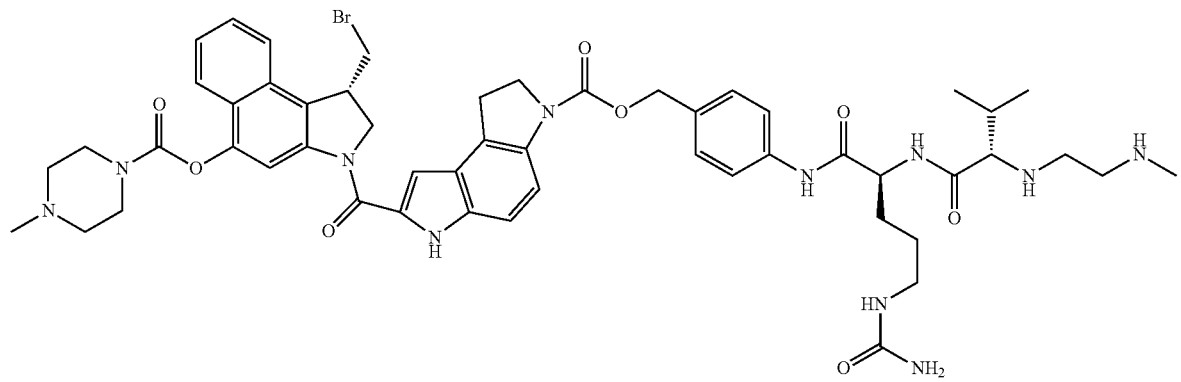
formula (n)
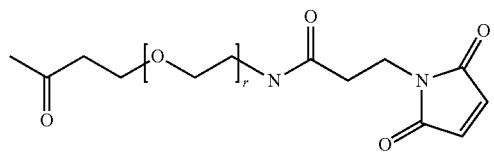
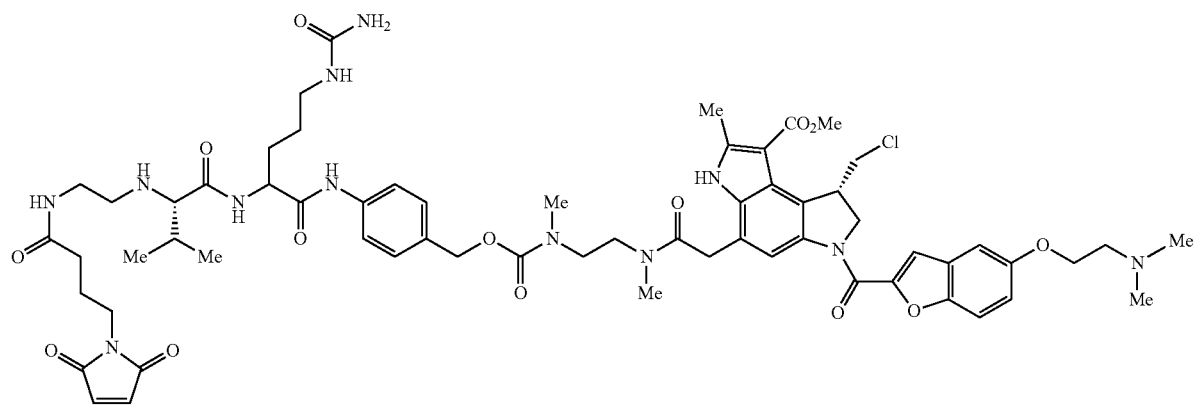
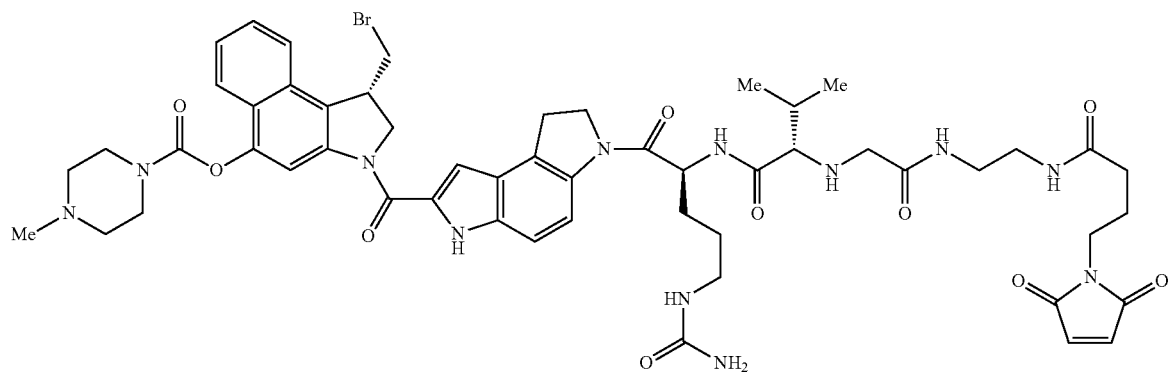

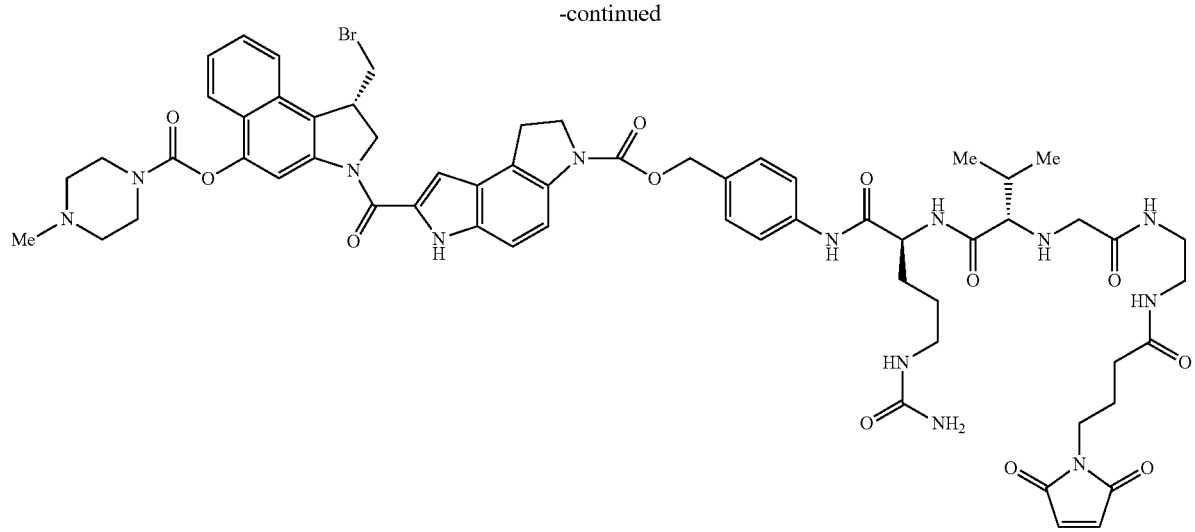
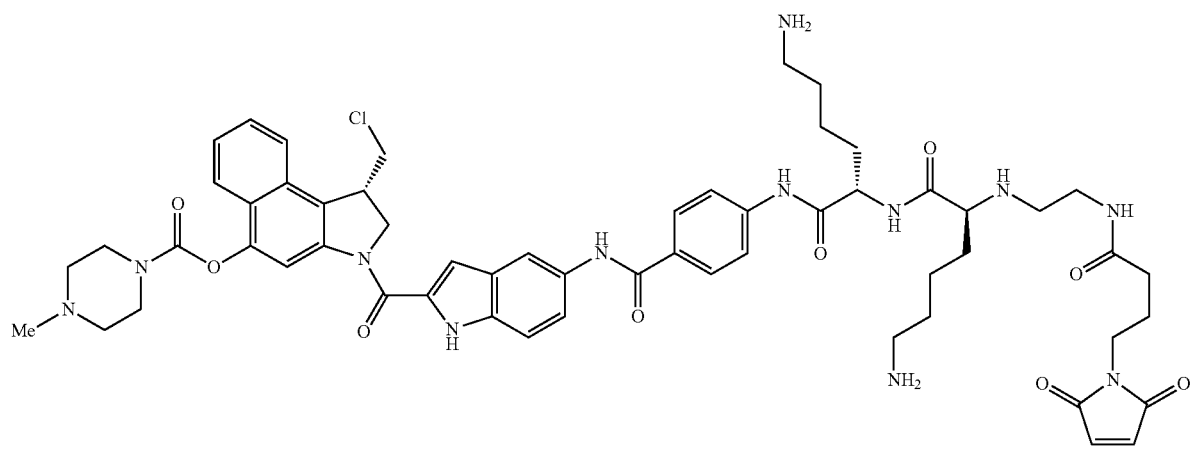
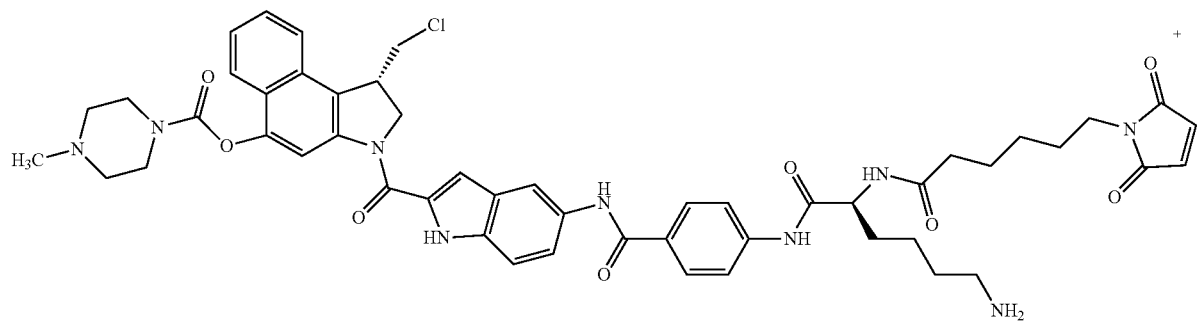
In the foregoing compounds, where the subscript r is present in a formula, it is an integer in the range of 0 to 24. R, wherever it occurs, is
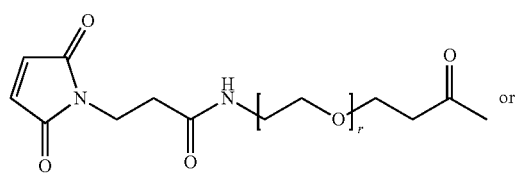 or 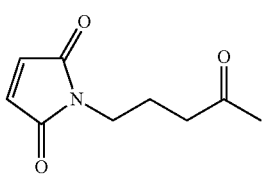
Each of the foregoing compounds has a maleimide group and is ready for conjugation to an antibody via a cysteine sulfhydryl group on the C-terminal heavy chain extension.

Nucleic Acid Molecules Encoding Antibodies of the Invention

Another aspect of the invention pertains to nucleic acid molecules that encode the antibodies of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once nucleic acids encoding a heavy chain of the antibody of interest is obtained, these nucleic acids can be further manipulated by standard recombinant DNA techniques. For example, well known site directed mutagenesis techniques, such as those described in the examples below, can be employed to introduce a cysteine to the C-terminus of the heavy chain of the antibody. Introduction of the cysteine can occur at the original C-terminal position of the heavy chain, or can occur by the incorporation of an extension to the original C-terminus of the heavy chain. Unless specified otherwise, a C-terminal extension is not limited so long as it contains a cysteine residue and allows for the conjugation to a partner molecule.

In certain embodiments, the C-terminal extensions will include, or consist of, a peptide that includes a cysteine residue. In preferred embodiments, the C-terminal extension peptides will be selected such that they do not act as protease substrates. Furthermore, the C-terminal extension peptides can be preferentially selected so as to not be immunogenic or antigenic to the intended recipient. In such embodiments the peptide will contain from about 1 amino acid to about 20 amino acids, with extensions of 1, 2, 3, 4, 5, 6, 7, 8, 9, and 10 amino acids being preferred. Such extensions preferably comprise, in addition to at least one cysteine residue, neutral amino acids with small side chains suc as alanine, glycine, valine, leucine, isoleucine, and methionine. In preferred embodiments, the C-terminal extension contains an amino acid sequence motif selected from a group comprising C, CX, XC, CXX, XCX, XXC, CXXX, XCXX, XXCX, XXXC, CXXXX, XCXXX, XXCXX, XXXCX, or XXXXC, wherein X is a cysteine residue or a neutral amino acid with a small side chain.

In one embodiment, the C-terminal extension is Cys-Ala-Ala. In another embodiment, the C-terminal extension is Cys-Cys-Ala-Ala (SEQ ID NO:9). In another embodiment, the C-terminal extension is Ala-Ala-Cys-Ala-Ala (SEQ ID NO:7). In another embodiment, the C-terminal extension is Gly-Gly-Gly-Gly-Ser-Cys-Ala-Ala (SEQ ID NO:8).

Production of Monoclonal Antibodies

Monoclonal antibodies (mAbs) of the present invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of the invention are human monoclonal antibodies. Such human monoclonal antibodies directed against potential targets can be generated using transgenic or transchromosomic mice carrying parts of the human immune system rather than the mouse system. These transgenic and transchromosomic mice include mice referred to herein as the HUMAB MOUSE® and KM MOUSE® mice, respectively, and are collectively referred to herein as "human Ig mice."

The HUMAB MOUSE® transgenic mouse (Medarex®, Inc.) contains human immunoglobulin gene miniloci that encode unrearranged human heavy ($\mu$ and $\gamma$) and $\kappa$ light chain immunoglobulin sequences, together with targeted mutations that inactivate the endogenous $\mu$ and $\kappa$ chain loci (see e.g., Lonberg, et al. (1994) Nature 368(6474): 856-859). Accordingly, the mice exhibit reduced expression of mouse IgM or $\kappa$, and in response to immunization, the introduced human heavy and light chain transgenes undergo class switching and somatic mutation to generate high affinity human IgG$\kappa$ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-30; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569, 825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al., each of which is also incorporated by reference.

In another embodiment, human antibodies of the invention can be raised using a mouse that carries human immunoglobulin sequences on transgenes and transchomosomes, such as a mouse that carries a human heavy chain transgene and a human light chain transchromosome. This mouse is referred to herein as a "KM MOUSE® transchromosomic mouse" and is described in detail in PCT Publication WO 02/43478 to Ishida et al.

Still further, alternative transgenic animal systems expressing human immunoglobulin genes are available in the art and can be used to raise the antibodies of the invention. For example, an alternative transgenic system referred to as the XENOMOUSE™ mouse (Amgen, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise antibodies to the target of choice. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and PCT application No. WO/2002/092812 and can be used to raise antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

When human Ig mice are used to raise human antibodies of the invention, such mice can be immunized with a purified or enriched preparation of target antigen and/or recombinant target protein, or cells expressing the target protein, or a target fusion protein, as described by Lonberg, N. et al. (1994) Nature 368(6474): 856 859; Fishwild, D. et al. (1996) Nature Biotechnology 14: 845-851; and PCT Publication WO 98/24884 and WO 01/14424. Preferably, the mice will be 6-16 weeks of age upon the first infusion. For example, a purified or recombinant preparation (5-50 µg) of target antigen can be used to immunize the human Ig mice intraperitoneally.

Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-target human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM MOUSE® strain can be used.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CYTOPULSE™ large chamber cell fusion electroporator (CytoPulse Sciences, Inc., Glen Burnie Md.). Cells are plated at approximately 2×105 in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2 mercaptoethanol, 50 units/ml penicillin, 50 mg/ml streptomycin, 50 mg/ml gentamycin and 1× HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A SEPHAROSE™ column (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VK segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and ChasM, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Bispecific Molecules

In another aspect, the present invention features bispecific molecules comprising an antibody of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for a first and a second binding specificity for a second target epitope. In a particular embodiment of the invention, the second target epitope is an Fc receptor, e.g., human Fc*RI (CD64) or a human Fca receptor (CD89). Therefore, the invention includes bispecific molecules capable of binding both to Fc*R or FcαR expressing effector cells (e.g., monocytes, macrophages or polymorphonuclear cells (PMNs)), and to target cells expressing the first target. These bispecific molecules target the first target expressing cells to effector cell and trigger Fc receptor-mediated effector cell activities, such as phagocytosis of first target expressing cells, antibody dependent cell-mediated cytotoxicity (ADCC), cytokine release, or generation of superoxide anion.

In another approach, the conjugates of the present invention are employed in a two-step targeting method. (Kraeber-Bodéré et al., Journal of Nuclear Medicine Vol. 47 No. 2 247-255 (2006); Saga et al., Cancer Research, 54, 2160-2165 (1994) both of which are hereby incorporated by reference in their entirety). In exemplary embodiments of this approach, the antibody of the antibody-partner conjugate functions to target the conjugate to a specific location via its binding specificity. The second step is achieved by introducing a binding molecule specific for the partner molecule of the antibody-partner conjugate. In such embodiments, high affinity binding systems, e.g., avidin-biotin, are employed as the partner molecule/binding molecule. In exemplary embodiments, the binding molecule specific for the partner molecule is conjugated to a radioisotope, toxin, marker, or theraputic agent.

In another approach, referred to as antibody-directed enzyme prodrug therapy (ADEPT), an enzyme is attached to an antibody specific for a tumor antigen, to thereby direct the enzyme to the site of tumor cells. The drug is then conjugated to a substrate cleavable by the enzyme attached to the tumor-specific antibody. Thus, these drug-cleavable substrate conjugates have tumor specificity arising from the localization of the enzyme at the site of tumor cells through the attachment of the enzyme to the tumor-specific antibody.

In an embodiment of the invention in which the bispecific molecule is multispecific, the molecule can further include a third binding specificity, in addition to an anti-Fc binding specificity and a first target binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of the invention comprise as a binding specificity at least one antibody.

In one embodiment, the binding specificity for an Fcγ receptor is provided by a monoclonal antibody, the binding of which is not blocked by human immunoglobulin G (IgG). As used herein, the term "IgG receptor" refers to any of the eight *-chain genes located on chromosome 1. These genes encode a total of twelve transmembrane or soluble receptor isoforms which are grouped into three Fc* receptor classes: Fc*RI (CD64), Fc*RII (CD32), and Fc*RIII (CD16). In one preferred embodiment, the Fcγ receptor a human high affinity Fc*RI. The human Fc*RI is a 72 kDa molecule, which shows high affinity for monomeric IgG (108-109 M-1).

The production and characterization of certain preferred anti-Fcγ monoclonal antibodies are described in PCT Publication WO 88/00052 and in U.S. Pat. No. 4,954,617 to Fanger et al., the teachings of which are fully incorporated by reference herein. These antibodies bind to an epitope of Fc*RI, Fc*RII or Fc*RIII at a site which is distinct from the Fc* binding site of the receptor and, thus, their binding is not blocked substantially by physiological levels of IgG. Specific anti-Fc*RI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fc* receptor antibody is a humanized form of monoclonal antibody 22 (H22). The production and characterization of the H22 antibody is described in Graziano, R. F. et al. (1995) J. Immunol. 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (Fc*RI (CD89)), the binding of which is preferably not blocked by human immunoglobulin A (IgA). The term "IgA receptor" is intended to include the gene product of one *-gene (Fc*RI) located on chromosome 19. This gene is known to encode several alternatively spliced transmembrane isoforms of 55 to 110 kDa. Fc*RI (CD89) is constitutively expressed on monocytes/macrophages, eosinophilic and neutrophilic granulocytes, but not on non-effector cell populations. Fc*RI has medium affinity ($\sim 5 \times 10^7$ M-1) for both IgA1 and IgA2, which is increased upon exposure to cytokines such as G-CSF or GM-CSF (Morton, H. C. et al. (1996) Critical Reviews in Immunology 16:423-440). Four Fc*RI-specific monoclonal antibodies, identified as A3, A59, A62 and A77, which bind Fc*RI outside the IgA ligand binding domain, have been described (Monteiro, R. C. et al. (1992) J. Immunol. 148: 1764).

Fc*RI and Fc*RI are preferred trigger receptors for use in the bispecific molecules of the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and first target binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies conjugated with a partner molecule, or antigen-binding portion(s) thereof, of the present invention, formulated together with a pharmaceutically acceptable carrier.

Pharmaceutical compositions of the invention also can be administered in combination therapy, i.e., combined with other agents. For example, the combination therapy can include an antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the conjugated antibody and partner molecule may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug). Preferably, the antibody-drug conjugate retards growth of the tumor when administered in the daily dosage amount over a period of at least five days. In at least some embodiments, the tumor is a human-type tumor in a SCID mouse. As an example, the SCID mouse can be a CB17.SCID mouse (available from Taconic, Germantown, N.Y.).

Alternatively, the antibody conjugate can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody conjugate of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 7,201,746, which discloses a variable flow implantable micro-infusion pump for dispensing medication at a controlled rate; U.S. Pat. No. 5,466,465, which discloses a therapeutic device for administering medicants through the skin; U.S. Pat. No. 6,742,992, which discloses a medication infusion pump for delivering medication at a precise infusion rate; U.S. Pat. No. 6,976,981, which discloses an osmotic drug delivery system having multi-chamber compartments. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Uses and Methods

The antibody conjugate compositions and methods of the present invention have numerous in vitro and in vivo diagnostic and therapeutic utilities involving the diagnosis and treatment of disorders mediated by the antigen to which the antibody expresses affinity. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles.

Suitable routes of administering the antibody conjugate compositions of the invention in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human antibody conjugates of the invention can be co-administered with one or other more therapeutic agents, e.g., a cytotoxic agent, a radiotoxic agent or an immunosuppressive agent. In addition to the antibody partner molecule, the partner molecule can also be administered separately. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of the antibodies, or antigen binding fragments thereof, of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

Also within the scope of the present invention are kits comprising the antibody conjugate compositions of the invention and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the antigen distinct from the first human antibody).

Accordingly, patients treated with antibody compositions of the invention can be additionally administered (prior to, simultaneously with, or following administration of a human antibody of the invention) with another therapeutic agent, such as a cytotoxic or radiotoxic agent, which enhances or augments the therapeutic effect of the human antibodies.

The present invention is further illustrated by the following examples which should not be construed as further limiting. The contents of all figures and all references, patents and published patent applications cited throughout this application are expressly incorporated herein by reference.

EXAMPLES

Example 1

Preparation of 2A10 Antibodies Having C-Terminal Cysteine Residues

Figure 2:
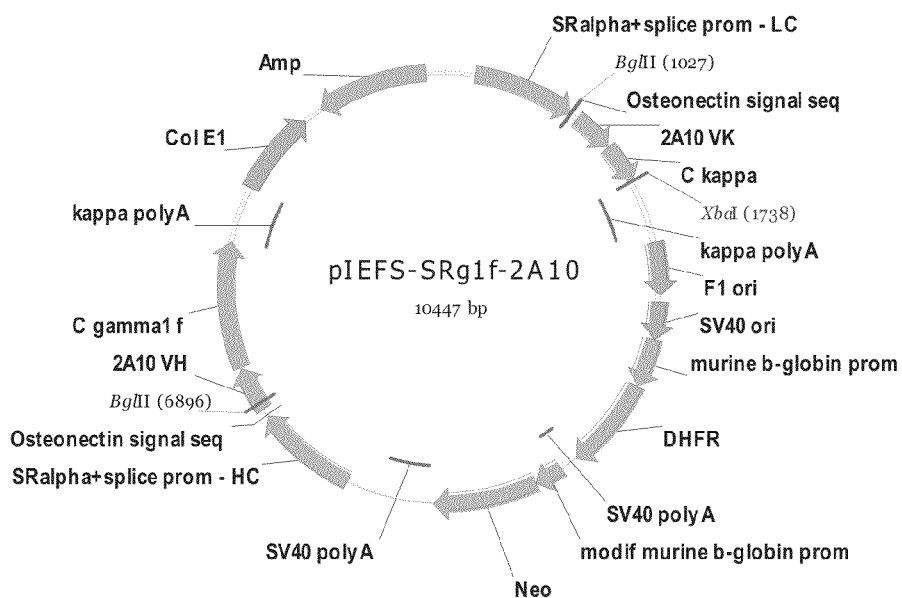
FIG. 2: pIEFs SRg1f-2A10 plasmid. Starting vector pIEFs SRg1f-2A10.

Vectors containing the 2A10 IgG1 antibody sequence were used as the starting point to make the antibodies having C-terminal cysteine residues (either near the original C-terminus or via the addition of a C-terminal extension). The two starting vectors were pICOFs-2A10 plasmid (FIG. 1) and pIEFs SRg1f-2A10 plasmid (FIG. 2).

In order to do site-directed mutagenesis on the human G1 constant region, the pICOFs-2A10 plasmid was digested SalI/NotI, and the band containing the 2A10 sequence was then isolated by agarose gel electrophoresis, followed by GeneClean purification. The purified fragment was ligated into the pBlueScript KS+ vector cut SalI/NotI, which was similarly purified. Clones from the transformation were screened by restriction digest of miniprep DNA. The same miniprep DNA was then used for the mutagenesis procedure.

Mutagenesis was done to add an extension composed of the amino acids CAA to the c-terminus of the Cgamma1f (2A10-CAA) or change the serine near the C-terminus (position 442) to a cysteine (2A10-C442). The Stratagene QuickChange Site-Directed Mutagenesis Kit was used with the following oligos made by Operon: 2A10S442Cfor: CAGAAGAGC-CTCTGCCTGTCCCCGGGTAAATGA (SEQ ID NO: 14), and 2A10S442Crev: TCATTTACCCGGGGACAGGCA-GAGGCTCTTCTG (SEQ ID NO: 15) for the C442 mutation and 2A10CAAfor: CTGTCCCCGGGTAAATGCAGCT-TGAGTGCGACGGCCG (SEQ ID NO: 16), and 2A10CAArev: CGGCCGTCGCACTCAAGCTGCACATT-TACCCGGGGACAG (SEQ ID NO: 17) for the CAA mutation.

Following the mutagenesis, miniprep DNA from 4 clones from each mutagenesis was produced by standard methods and sequenced for confirmation of the mutations. The chromatograms were analyzed using ChromasPro software and then the sequence was transferred to VectorNTI for further analysis. Correct clones were then digested BssHII/KpnI to isolate the 2A10 mutant heavy chain as previously described. The UCOE expression vector 153-118 was digested with AscI/PvuI and KpnI/PvuI, and the bands isolated and purified as before. A three way ligation was then performed using the two vector fragments and the 2A10 HC BssHII/KpnI fragment to construct the final expression vectors. Clones were screened by miniprep DNA restriction digest.

The 2A10 LC was cloned into the UCOE vector 153-117 in order to cotransfect with the 2A10 HC constructs. The pIEFs SRg1f-2A10 plasmid was digested with BglII/XbaI and the 2A10 LC band was isolated as previously described. The 153-117 MCS6 vector was digested with Xba/SspI and SspI/BamHI and bands isolated as before. A three-way ligation was done using the 2A10 LC band and the two 153-117 vector bands to construct the final 2A10 LC expression vector. Clone miniprep DNA was screened by restriction digest.

Qiagen Qiafilter Midipreps were done for each construct: 2A10 LC 153-117, 2A10 HC CAA 153-118 and 2A10 HC C442 153-118. The resulting DNA was resuspended in sterile dH2O and sequenced.

CHO—S cells were co-transfected with the 2A10 LC 153-117 plasmid and either the 2A10 HC CAA 153-118 or the 2A10 HC C442 153-118 plasmid, using DMRIE-C transfection reagent and the manufacturers recommended procedure. CHO—S transfectants were cultured in CD CHO media containing 8 mM Glutamine/1×HT/PenStrep until day 3 post transfection when they were placed under dual drug selection with 500 μg/ml each of G418 and Hygromycin. At this time cells were plated into 96-well plates and serially diluted in order to raise isolated clones for each transfectant.

After the clones in the 96-well plates were nearly confluent, supernatant was taken from each well and screened for human IgG expression by ELISA (FIG. 3). CHO 2A10 CAA #1 and CHO 2A10 C442 #14 were expanded to generate supernatant which could be used for antibody purification.

Example 2

Purification and Conjugation of C-terminal Cysteine Containing Antibodies to Toxin Both C-terminal cysteine containing control antibody 2A10-C442 and the 2A10-CAA antibody) were purified by protein A chromatography. Supernatant from CHO cells expressing each antibody was adjusted to approx. pH8.8, and loaded onto a protein A SEPHAROSE™ column pre-equilibrated with 50 mM glycine/glycinate buffer pH8.8. After washing the column with equilibration buffer, antibody was eluted with 0.1M citric acid pH3.5, and fractions containing antibody rapidly adjusted to pH7 and pooled. Antibody was then buffer exchanged into 50 mM acetate buffer pH5.5 for storage.

For site-specific conjugation to formula (n), antibodies were buffer exchanged into 100 mM phosphate buffer, 50 mMNaCl, 2 mMDTPA, pH6 and the thiol activated with 4.5 mM cysteamine, followed by incubation for 30 minutes at 37° C. Following activation antibodies were buffer exchanged into 50 mM HEPES buffer, containing 5 mM glycine, 2 mMDTPA and 0.5% povidone(10K), at pH5.5. Thiol activation was verified by assay with 4,4'-dithiodipyridine, measuring thiopyridine released at 324 nM. Site-specific conjugation of CAA was achieved by addition of formula (n) at a 3 fold molar excess with a final concentration of 10% DMSO in the reaction mix. After 90 minutes incubation at room temperature, the resulting conjugate was purified by size exclusion chromatography on a SUPERDEX 200™ column run in 50 mM HEPES, 5 mM glycine, 100 mM NaCl, pH7.2.

Thiol assays for the two C-terminal cysteine containing antibodies revealed comparable values of approx. 2 as expected for the one cysteine introduced onto each of the two heavy chains of the assembled antibody.

Example 3

Antigen Binding and Cytotoxicity of 2A10-CAA Antibody

Antigen binding was measured in a standard ELISA format assay, using plates coated with 10 μg/ml of PSMA. Bound antibody was detected with goat anti-human IgG F(ab')2 fragment conjugated to HRP, and signal developed using TMB.

Figure 6:
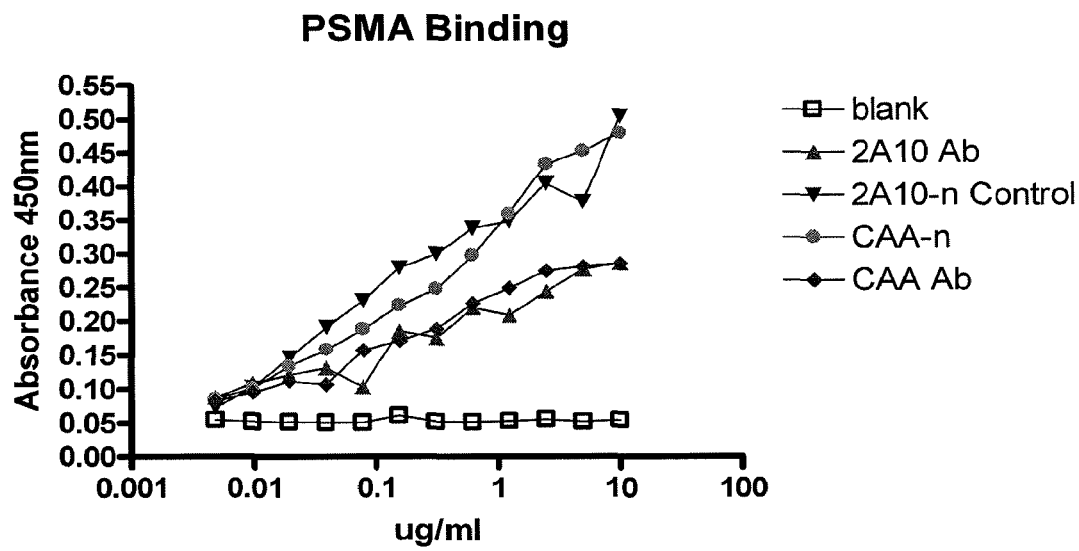
FIG. 6: Antigen Binding ELISA. Antigen (PSMA) binding measured in a standard ELISA format assay. Bound antibody detected with goat anti-human IgG F(ab')$_2$ fragment conjugated to HRP, and signal developed using TMB.

Results showed identical binding of the CAA antibody to the parental antibody control. In addition, the conjugated CAA antibody showed identical binding as the randomly conjugated antibody control (FIG. 6)

Figure 7:
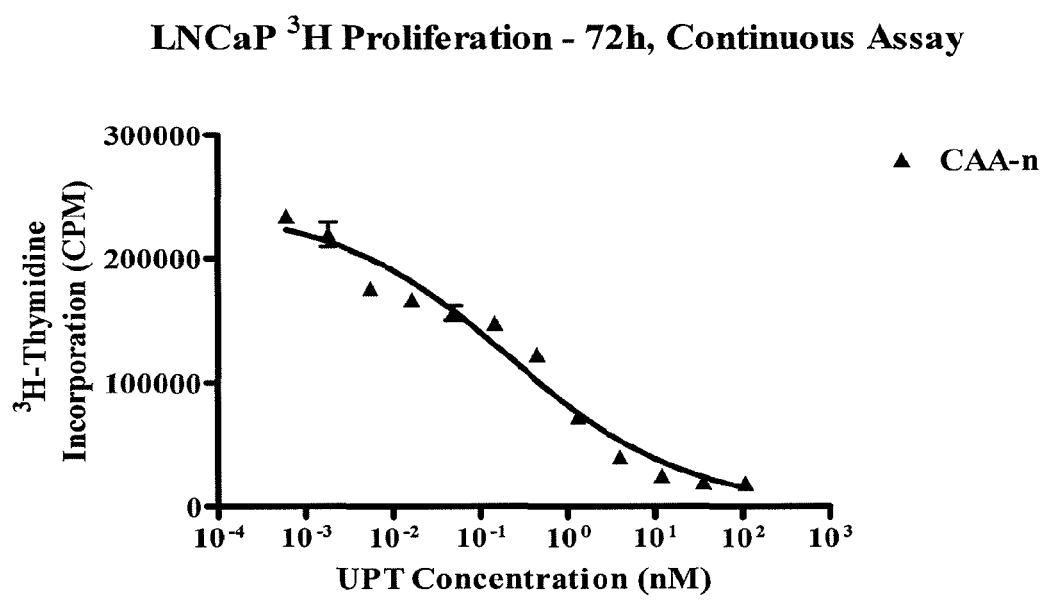
FIG. 7: Cytotoxicity assay. Cytotoxicity of antibodies determined in a standard tritiated thymidine proliferation assay using PSMA-expressing LNCaP cells.

Cytotoxicity was determined in a standard tritiated thymidine proliferation assay using LNCaP cells. LNCaP express high levels of PSMA on the cell surface. Incubation of the cells with conjugate was carried out for 72 hours. Results showed that the CAA variant conjugate with formula (n) was potent in inhibiting proliferation of target cells with an EC50 of 0.22 nM in this assay (FIG. 7).

Example 4

Construction of CD70.1 CAA

Vector 2A10 CAA pBlueScript KS+ (previously described) was digested with NotI/NheI to remove the 2A10 VH region, and the remaining vector band was agarose gel purified. pICO CD70.1.4 was digested NotI/NheI to cut out the CD70.1 VH region which was isolated from the vector by agarose gel. CD70.1 VH(NotI/NheI) was cloned into CAA pBlueScript KS+(NotI/NheI). The resulting CD70.1 CAA IgG heavy chain was then cloned into pICOFSCpurG for heavy chain expression. The resulting vector was named CD70CAA pFSCG.

pICO CD70.1.4 was digested with BglII/BsiWI to cut out the CD70.1 Vk region, which was then gel purified. The human Ig kappa chain expression vector pICOFSCneok was digested BglII/BsiWI and the cut vector was gel purified. The CD70.1 Vk BglII/BsiWI fragment was then cloned into pICOFSCneok (BglII/BsiWI) for light chain expression. The resulting vector was named CD70VLpFSCN.

Qiagen Qiafilter Midipreps were done for each construct: CD70VLpFSCN, and CD70CAA pFSCG. The resulting purified plamids were resuspended in sterile $dH_2O$ and sequenced to verify the correct sequences.

Figure 8:
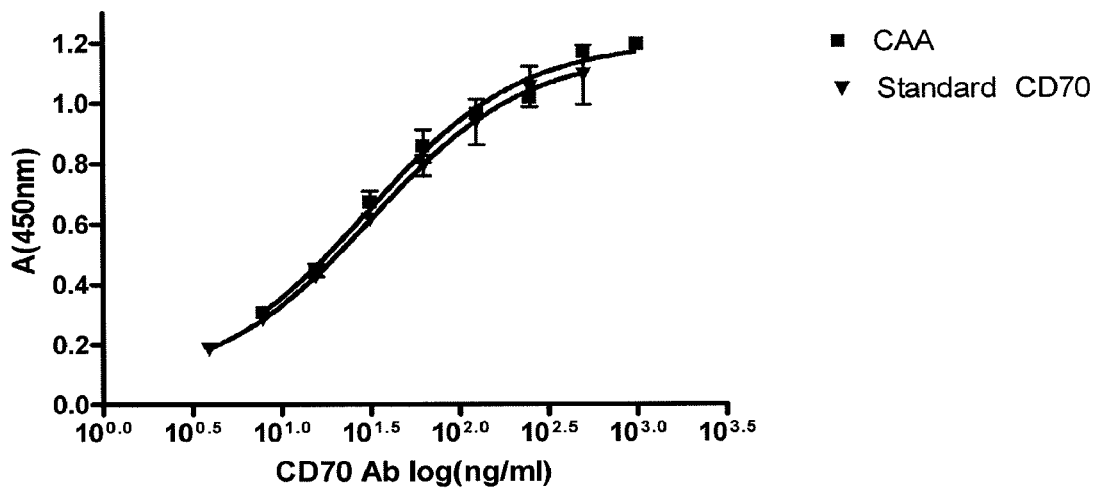
FIG. 8: Antigen Binding ELISA. Antigen binding measured in using plates coated with recombinant CD70-mouse Fc fusion protein. Bound antibody detected with anti-human IgG Fc fragment conjugated to HRP.

CHO—S cells were co-transfected with the CD70VLpFSCN plasmid and the CD70CAA pFSCG using the Amaxa suspension CHO cell program with the manufacturers recommended procedure. CHO—S transfectants were cultured in CD CHO media containing 8 mM Glutamine/1× HT/PenStrep until day 3 post transfection when they were placed under dual drug selection with 500 µg/ml G418 and 4 µg/ml Puromycin. At this time cells were plated into 96-well plates and serially diluted in order to raise isolated clones. After the clones in the 96-well plates were nearly confluent, supernatant was taken from each well and screened for human IgG expression by ELISA. A high expressing clone was identified and expanded to provide supernatant containing the antibody CD70-CAA. CD70-CAA was purified by standard techniques and tested for binding to CD70 by ELISA. ELISA was carried out by standard techniques using plates coated with recombinant CD70-mouse Fc fusion protein and after titration of anti-CD70 antibody, detection with anti-human IgG Fc specific antibody conjugated with horseradish peroxidase. No difference in binding was observed compared to the parental antibody (FIG. 8).

Example 5

Construction of Antibody Variants with C-Terminal Extensions

The sequences AACAA, GGGGSCAA and CCAA were also constructed as C-terminal extensions to the CD70 antibody. In order to introduce these sequences to the 3' end of the anti-CD70 heavy chain constant region, the following primers were used: CD70.1-AACAA (SEQ ID NO:7) anti-sense primer, 5' cactctcccctggatcctcatgcggcg-caagcggctttacccggggacagggagaggctcttctg-3' (SEQ ID NO:18); CD70.1-CCAA (SEQ ID NO:9) anti-sense primer, 5'-cactctccectggatectcaagctgca-cagcatttacccggggacagggagaggacttctg-3' (SEQ ID NO:19); and CD70.1-G$_4$SCAA (SEQ ID NO:8) anti-sense primer, 5'-cactctcccctggatcctcaagctgcg-caggaaccgcceccacctttacccggggacagggagaggctcttctg-3' (SEQ ID NO:20). The forward primers for all above three variants are the same: 5% tccaccgcggtggeggccgccaccatg-gagtttgggctgagctgggnttectcgttgct-3' (SEQ ID NO:21). The forward primer contained a NotI site and the reverse primers all contained BamHI sites. PCR was then performed using cloned pfu DNA polymerase (Invitrogen). These PCR products were cloned into pICOFSCpurG digested by NotI and BamHI. All constructs were sequenced to confirm sequence fidelity.

Stable cell lines expressing the CD70 antibody variants were established by co-transfection of the light and heavy chain constructs in an equimolar ratio into CHOS cells, using DMRIEC transfection reagent (Invitrogen) according to the manufacturer's instructions. Three days after, transfected cells were selected under 4 µm/ml puromycin and 500 µm/ml G418. Stable clones were isolated by limited dilution in 96-well plates. To screen puromycin/G418-resistant clones for their ability to secrete the antibody mutants, supernatants of transfectant cells were tested by ELISA. Briefly, MAX-ISORB™ 96-well plates (Nunc, Roskilde, Denmark) were coated with 5 µg/ml rabbit anti-human kappa antibody in 0.5 M sodium carbonate buffer (pH 9.7) for 16 h at 4° C. After blocking for 1 h with SUPER BLOCK™ protein block (ScyTeK Laboratories) at room temperature, isolated supernatants were added in 1/2 sequential dilutions, and incubated for 1 h at room temperature. Plates were subsequently washed three times and incubated with HRP-conjugated rabbit anti-human gamma specific antibody (Jackson research laboratories) for 1 h at room temperature. After washing, plates were developed with TMB peroxidase EIA substrate kit (Bio-Rad). The reaction was stopped with 2 M $H_2SO_4$, and OD was measured at 450 nm. Positive cells were further expanded and the expression was confirmed by ELISA.

Figure 9:
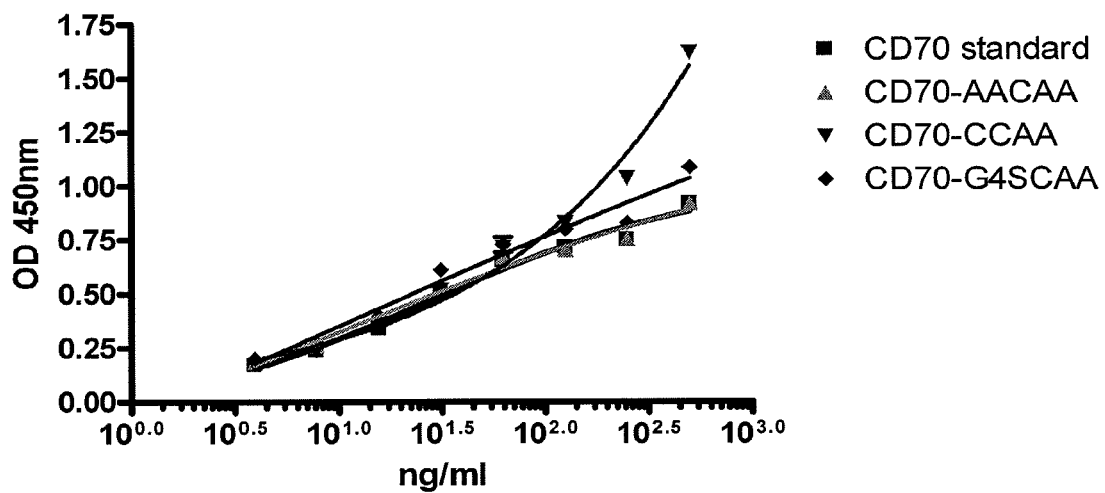
FIG. 9: Antigen Binding ELISA. Antigen binding by antibody variants with AACAA (SEQ ID N07), GGGGSCAA (SEQ ID NO:8), and CCAA (SEQ ID NO:9) C-terminal extensions were measured in a standard ELISA format assay.

High expressing stable clones were identified and scaled up to produce supernatant containing each antibody, which were then purified by standard techniques. Binding to CD70 was tested by ELISA as described above and all variants demonstrated good binding to the antigen demonstrating no effect of the C-terminal addition on antigen binding properties (FIG. 9)

Conjugation to the DNA minor-groove binding alkylating agent (MGBA) formula (m) was carried out for each antibody in the same manner as described above for conjugation of MGBA to anti-PSMA antibody. Compounds reacted specifically with the C-terminal added sequences. Conjugates with each variant were able to induce specific cytotoxicity of CD70 positive 786-0 cells in an equivalent manner to randomly conjugated CD70 antibody (FIG. 3). A control conjugate with PSMA antibody linked to formula (m) was unable to induce cytotoxicity of 786-0 cells, demonstrating the specific manner of the cell killing.

Figure 11:
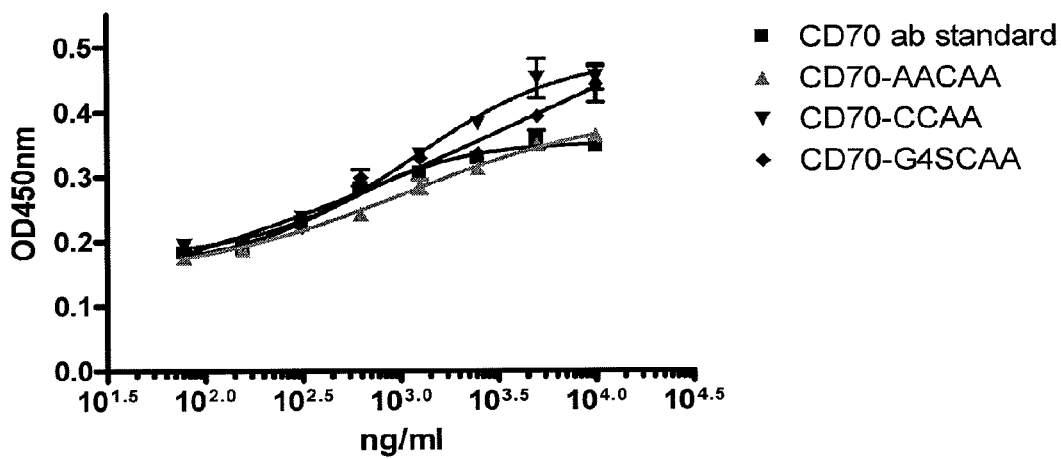
FIG. 11: Antigen Binding ELISA. ELISA assay results for assay monitoring antigen binding using plates coated with Cd16.

Human IgG1 antibodies to CD70 are also able to mediate CD16 dependent antibody-dependent cellular cytotoxicity. To verify that this beneficial property of the antibodies was not altered with antibodies with C-terminal extensions, a CD16 binding ELISA was carried out by standard techniques. Results (FIG. 11), demonstrate no loss of CD16 binding for the variant antibodies.

The above mentioned patents, published patent applications, test methods, and non-patent publications are hereby incorporated by reference in their entirety. Furthermore, any variations of the present invention will suggest themselves to those skilled in the art in light of the above detailed description. All such variations are within the fully intended scope of the appended claims.

The invention claimed is:

1. An antibody-partner molecule conjugate comprising a full-length antibody conjugated to a partner molecule wherein the conjugation occurs via a cysteine-containing extension at the C-terminus of a heavy chain of the antibody, wherein said cysteine-containing extension has an amino acid sequence selected from the group consisting of CAA, CCAA (SEQ ID NO:9), AACAA (SEQ ID NO:7), and GGGGSCAA (SEQ ID NO:8).

2. The antibody-partner molecule conjugate of claim 1 wherein the cysteine-containing extension is introduced by the addition of a cysteine-containing extension to the heavy chain of the antibody.

3. The antibody-partner molecule conjugate of claim 1 wherein the C-terminal cysteine-containing extension is introduced by the replacement of the original C-terminal amino acid residue of the heavy chain of the antibody.

4. The antibody-partner molecule conjugate of claim 1, wherein the partner molecule is a cytotoxic drug.

5. The antibody-partner molecule conjugate of claim 4, wherein the drug is selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid.

6. The antibody-partner molecule conjugate of claim 1, further comprising a cleavable linker.

7. The antibody-partner molecule conjugate of claim 6, wherein the linker is a peptide linker cleavable by an intracellular protease.

8. The antibody-partner molecule conjugate of claim 7, wherein the peptide linker is a val-cit linker or a phe-lys linker.

9. An antibody-drug conjugate comprising:
   a full length antibody that:
   (a) binds to PSMA, and
   (b) is conjugated to a cytotoxic agent or an immunosuppressive agent,
   wherein the antibody-drug conjugate exerts:
   (a) a cytotoxic or cytostatic effect on a PSMA-expressing cancer cell line, or
   (b) a cytotoxic, cytostatic, or immunosuppressive effect on a PSMA-expressing immune cell,
   wherein the conjugation occurs at an introduced cysteine residue at or near the C-terminus of a heavy chain of the antibody, wherein said introduced cysteine residue is in a C-terminal cysteine-containing extension having an amino acid sequence selected from CAA, CCAA (SEQ ID NO:9), AACAA (SEQ ID NO:7), and GGGGSCAA (SEQ ID NO:8).

10. A method of making an antibody-partner molecular conjugate, comprising the steps of:
   (a) providing a full-length antibody;
   (b) modifying the C-terminus of at least one of the heavy chains of the full-length antibody by adding thereto a cysteine-containing extension having an amino acid sequence selected from the group consisting of CAA, CCAA (SEQ ID NO:9), AACAA (SEQ ID NO:7), and GGGGSCAA (SEQ ID NO:8); and
   (c) conjugating the modified full-length antibody to a partner molecule via the cysteine residue of the cysteine-containing extension.

11. A full length antibody, wherein the C-terminus of at least one of its heavy chains has been modified by adding thereto a cysteine-containing extension having an amino acid sequence selected from the group consisting of CAA, CCAA (SEQ ID NO:9), AACAA (SEQ ID NO:7), and GGGGSCAA (SEQ ID NO:8).

* * * * *

SEQUENCE LISTING

```
<160> NUMBER OF SEQ ID NOS: 21

<210> SEQ ID NO 1
<211> LENGTH: 466
<212> TYPE: PRT
<213> ORGANISM: Homo sapiens

<400> SEQUENCE: 1

Met Arg Ala Trp Ile Phe Phe Leu Leu Cys Leu Ala Gly Arg Ala Leu
1               5                   10                  15

Ala Glu Val Gln Leu Val Gln Ser Gly Ala Glu Val Lys Lys Pro Gly
            20                  25                  30

Glu Ser Leu Lys Ile Ser Cys Lys Gly Ser Gly Tyr Ser Phe Thr Ser
        35                  40                  45

Asn Trp Ile Gly Trp Val Arg Gln Met Pro Gly Lys Gly Leu Glu Trp
    50                  55                  60

Met Gly Ile Ile Tyr Pro Gly Asp Ser Asp Thr Arg Tyr Ser Pro Ser
65                  70                  75                  80

Phe Gln Gly Gln Val Thr Ile Ser Ala Asp Lys Ser Ile Ser Thr Ala
                85                  90                  95

Tyr Leu Gln Trp Ser Ser Leu Lys Ala Ser Asp Thr Ala Met Tyr Tyr
            100                 105                 110

Cys Ala Arg Gln Thr Gly Phe Leu Trp Ser Ser Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335
```

```
Glu Tyr Lys Cys Lys Val Ser Asn Lys Ala Leu Pro Ala Pro Ile Glu
                340                 345                 350

Lys Thr Ile Ser Lys Ala Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 2
<211> LENGTH: 469
<212> TYPE: PRT
<213> ORGANISM: Homo sapiens

<400> SEQUENCE: 2

Met Arg Ala Trp Ile Phe Phe Leu Leu Cys Leu Ala Gly Arg Ala Leu
1               5                   10                  15

Ala Glu Val Gln Leu Val Gln Ser Gly Ala Glu Val Lys Lys Pro Gly
            20                  25                  30

Glu Ser Leu Lys Ile Ser Cys Lys Gly Ser Gly Tyr Ser Phe Thr Ser
        35                  40                  45

Asn Trp Ile Gly Trp Val Arg Gln Met Pro Gly Lys Gly Leu Glu Trp
    50                  55                  60

Met Gly Ile Ile Tyr Pro Gly Asp Ser Asp Thr Arg Tyr Ser Pro Ser
65                  70                  75                  80

Phe Gln Gly Gln Val Thr Ile Ser Ala Asp Lys Ser Ile Ser Thr Ala
                85                  90                  95

Tyr Leu Gln Trp Ser Ser Leu Lys Ala Ser Asp Thr Ala Met Tyr Tyr
            100                 105                 110

Cys Ala Arg Gln Thr Gly Phe Leu Trp Ser Ser Asp Leu Trp Gly Arg
        115                 120                 125

Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Arg Val Glu Pro Lys Ser Cys Asp
225                 230                 235                 240
```

-continued

```
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Ser Leu Ser Pro
    450                 455                 460
Gly Lys Cys Ala Ala
465

<210> SEQ ID NO 3
<211> LENGTH: 466
<212> TYPE: PRT
<213> ORGANISM: Homo sapiens

<400> SEQUENCE: 3

Met Arg Ala Trp Ile Phe Phe Leu Leu Cys Leu Ala Gly Arg Ala Leu
1               5                   10                  15
Ala Glu Val Gln Leu Val Gln Ser Gly Ala Glu Val Lys Lys Pro Gly
            20                  25                  30
Glu Ser Leu Lys Ile Ser Cys Lys Gly Ser Gly Tyr Ser Phe Thr Ser
        35                  40                  45
Asn Trp Ile Gly Trp Val Arg Gln Met Pro Gly Lys Gly Leu Glu Trp
    50                  55                  60
Met Gly Ile Ile Tyr Pro Gly Asp Ser Asp Thr Arg Tyr Ser Pro Ser
65                  70                  75                  80
Phe Gln Gly Gln Val Thr Ile Ser Ala Asp Lys Ser Ile Ser Thr Ala
                85                  90                  95
Tyr Leu Gln Trp Ser Ser Leu Lys Ala Ser Asp Thr Ala Met Tyr Tyr
            100                 105                 110
Cys Ala Arg Gln Thr Gly Phe Leu Trp Ser Ser Asp Leu Trp Gly Arg
        115                 120                 125
Gly Thr Leu Val Thr Val Ser Ser Ala Ser Thr Lys Gly Pro Ser Val
    130                 135                 140
```

```
Phe Pro Leu Ala Pro Ser Ser Lys Ser Thr Ser Gly Gly Thr Ala Ala
145                 150                 155                 160
Leu Gly Cys Leu Val Lys Asp Tyr Phe Pro Glu Pro Val Thr Val Ser
                165                 170                 175
Trp Asn Ser Gly Ala Leu Thr Ser Gly Val His Thr Phe Pro Ala Val
            180                 185                 190
Leu Gln Ser Ser Gly Leu Tyr Ser Leu Ser Ser Val Val Thr Val Pro
        195                 200                 205
Ser Ser Ser Leu Gly Thr Gln Thr Tyr Ile Cys Asn Val Asn His Lys
    210                 215                 220
Pro Ser Asn Thr Lys Val Asp Lys Arg Val Glu Pro Lys Ser Cys Asp
225                 230                 235                 240
Lys Thr His Thr Cys Pro Pro Cys Pro Ala Pro Glu Leu Leu Gly Gly
                245                 250                 255
Pro Ser Val Phe Leu Phe Pro Pro Lys Pro Lys Asp Thr Leu Met Ile
            260                 265                 270
Ser Arg Thr Pro Glu Val Thr Cys Val Val Val Asp Val Ser His Glu
        275                 280                 285
Asp Pro Glu Val Lys Phe Asn Trp Tyr Val Asp Gly Val Glu Val His
    290                 295                 300
Asn Ala Lys Thr Lys Pro Arg Glu Glu Gln Tyr Asn Ser Thr Tyr Arg
305                 310                 315                 320
Val Val Ser Val Leu Thr Val Leu His Gln Asp Trp Leu Asn Gly Lys
                325                 330                 335
Glu Tyr Lys Cys Lys Val Ser Asn Lys Ala Leu Pro Ala Pro Ile Glu
            340                 345                 350
Lys Thr Ile Ser Lys Ala Lys Gly Gln Pro Arg Glu Pro Gln Val Tyr
        355                 360                 365
Thr Leu Pro Pro Ser Arg Glu Glu Met Thr Lys Asn Gln Val Ser Leu
    370                 375                 380
Thr Cys Leu Val Lys Gly Phe Tyr Pro Ser Asp Ile Ala Val Glu Trp
385                 390                 395                 400
Glu Ser Asn Gly Gln Pro Glu Asn Asn Tyr Lys Thr Thr Pro Pro Val
                405                 410                 415
Leu Asp Ser Asp Gly Ser Phe Phe Leu Tyr Ser Lys Leu Thr Val Asp
            420                 425                 430
Lys Ser Arg Trp Gln Gln Gly Asn Val Phe Ser Cys Ser Val Met His
        435                 440                 445
Glu Ala Leu His Asn His Tyr Thr Gln Lys Ser Leu Cys Leu Ser Pro
    450                 455                 460
Gly Lys
465

<210> SEQ ID NO 4
<211> LENGTH: 1401
<212> TYPE: DNA
<213> ORGANISM: Homo sapiens

<400> SEQUENCE: 4
atgagggctt ggatcttctt tctgctctgc ctggccggga gagcgctcgc agaggtgcag      60
ctggtgcagt ctggagcaga ggtgaaaaag cccggggagt ctctgaagat ctcctgtaag     120
ggttctggat acagctttac cagtaactgg atcggctggg tgcgccagat gcccgggaaa     180
ggcctggagt ggatggggat catctatcct ggtgactctg ataccagata cagcccgtcc     240
```

```
ttccaaggcc aggtcaccat ctcagccgac aagtccatca gcaccgccta cctgcagtgg      300
agcagcctga aggcctcgga caccgccatg tattactgtg cgaggcaaac tggtttcctc      360
tggtcctccg atctctgggg ccgtggcacc ctggtcactg tctcctcagc tagcaccaag      420
ggcccatcgg tcttcccccct ggcaccctcc tccaagagca cctctggggg cacagcggcc     480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtg gacaagagag ttgagcccaa atcttgtgac      720
aaaactcaca catgcccacc gtgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
gtggtcagcg tcctcaccgt cctgcaccag gactggctga atggcaagga gtacaagtgc     1020
aaggtctcca acaaagccct cccagccccc atcgagaaaa ccatctccaa agccaaaggg     1080
cagccccgag aaccacaggt gtacaccctg cccccatccc gggaggagat gaccaagaac     1140
caggtcagcc tgacctgcct ggtcaaaggc ttctatccca gcgacatcgc cgtggagtgg     1200
gagagcaatg ggcagccgga gaacaactac aagaccacgc ctcccgtgct ggactccgac     1260
ggctccttct tcctctatag caagctcacc gtggacaaga gcaggtggca gcaggggaac     1320
gtcttctcat gctccgtgat gcatgaggct ctgcacaacc actacacgca gaagagcctc     1380
tccctgtccc cgggtaaatg a                                                1401

<210> SEQ ID NO 5
<211> LENGTH: 1410
<212> TYPE: DNA
<213> ORGANISM: Homo sapiens

<400> SEQUENCE: 5
atgagggctt ggatcttctt tctgctctgc ctggccggga gagcgctcgc agaggtgcag       60
ctggtgcagt ctggagcaga ggtgaaaaag cccggggagt ctctgaagat ctcctgtaag      120
ggttctggat acagctttac cagtaactgg atcggctggg tgcgccagat gcccgggaaa      180
ggcctggagt ggatggggat catctatcct ggtgactctg ataccagata cagcccgtcc      240
ttccaaggcc aggtcaccat ctcagccgac aagtccatca gcaccgccta cctgcagtgg      300
agcagcctga aggcctcgga caccgccatg tattactgtg cgaggcaaac tggtttcctc      360
tggtcctccg atctctgggg ccgtggcacc ctggtcactg tctcctcagc tagcaccaag      420
ggcccatcgg tcttcccccct ggcaccctcc tccaagagca cctctggggg cacagcggcc     480
ctgggctgcc tggtcaagga ctacttcccc gaaccggtga cggtgtcgtg gaactcaggc      540
gccctgacca gcggcgtgca caccttcccg gctgtcctac agtcctcagg actctactcc      600
ctcagcagcg tggtgaccgt gccctccagc agcttgggca cccagaccta catctgcaac      660
gtgaatcaca agcccagcaa caccaaggtg gacaagagag ttgagcccaa atcttgtgac      720
aaaactcaca catgcccacc gtgcccagca cctgaactcc tggggggacc gtcagtcttc      780
ctcttccccc caaaacccaa ggacaccctc atgatctccc ggacccctga ggtcacatgc      840
gtggtggtgg acgtgagcca cgaagaccct gaggtcaagt tcaactggta cgtggacggc      900
gtggaggtgc ataatgccaa gacaaagccg cgggaggagc agtacaacag cacgtaccgt      960
```

```
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct cctctatag caagctcacc gtggacaaga gcaggtggca gcaggggaac    1320
gtcttctcat gctccgtgat gcatgaggct ctgcacaacc actacacgca gaagagcctc    1380
tccctgtccc cgggtaaatg tgcagcttga                                    1410
```

<210> SEQ ID NO 6
<211> LENGTH: 1401
<212> TYPE: DNA
<213> ORGANISM: Homo sapiens

<400> SEQUENCE: 6

```
atgagggctt ggatcttctt tctgctctgc ctggccggga gagcgctcgc agaggtgcag      60
ctggtgcagt ctggagcaga ggtgaaaaag cccggggagt ctctgaagat ctcctgtaag     120
ggttctggat acagctttac cagtaactgg atcggctggg tgcgccagat gcccgggaaa     180
ggcctggagt ggatggggat catctatcct ggtgactctg ataccagata cagcccgtcc     240
ttccaaggcc aggtcaccat ctcagccgac aagtccatca gcaccgccta cctgcagtgg     300
agcagcctga aggcctcgga caccgccatg tattactgtg cgaggcaaac tggtttcctc     360
tggtcctccg atctctgggg ccgtggcacc ctggtcactg tctcctcagc tagcaccaag     420
ggcccatcgg tcttccccct ggcaccctcc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gctgtcctac agtcctcagg actctactcc     600
ctcagcagcg tggtgaccgt gccctccagc agcttgggca cccagaccta catctgcaac     660
gtgaatcaca agcccagcaa caccaaggtg gacaagagag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct cctctatag caagctcacc gtggacaaga gcaggtggca gcaggggaac    1320
gtcttctcat gctccgtgat gcatgaggct ctgcacaacc actacacgca gaagagcctc    1380
tgcctgtccc cgggtaaatg a                                              1401
```

<210> SEQ ID NO 7
<211> LENGTH: 5
<212> TYPE: PRT
<213> ORGANISM: Artificial Sequence
<220> FEATURE:
<223> OTHER INFORMATION: C-terminal extension

```
<400> SEQUENCE: 7

Ala Ala Cys Ala Ala
1               5

<210> SEQ ID NO 8
<211> LENGTH: 8
<212> TYPE: PRT
<213> ORGANISM: Artificial Sequence
<220> FEATURE:
<223> OTHER INFORMATION: C-terminal extension

<400> SEQUENCE: 8

Gly Gly Gly Gly Ser Cys Ala Ala
1               5

<210> SEQ ID NO 9
<211> LENGTH: 4
<212> TYPE: PRT
<213> ORGANISM: Artificial Sequence
<220> FEATURE:
<223> OTHER INFORMATION: C-terminal extension

<400> SEQUENCE: 9

Cys Cys Ala Ala
1

<210> SEQ ID NO 10
<211> LENGTH: 4
<212> TYPE: PRT
<213> ORGANISM: Artificial Sequence
<220> FEATURE:
<223> OTHER INFORMATION: Peptide conjugation sequence

<400> SEQUENCE: 10

Ala Leu Ala Leu
1

<210> SEQ ID NO 11
<211> LENGTH: 4
<212> TYPE: PRT
<213> ORGANISM: Artificial Sequence
<220> FEATURE:
<223> OTHER INFORMATION: Peptide conjugation sequence
<220> FEATURE:
<221> NAME/KEY: MOD_RES
<222> LOCATION: (1)..(1)
<223> OTHER INFORMATION: Residue 1 is beta alanine

<400> SEQUENCE: 11

Ala Leu Ala Leu
1

<210> SEQ ID NO 12
<211> LENGTH: 4
<212> TYPE: PRT
<213> ORGANISM: Artificial Sequence
<220> FEATURE:
<223> OTHER INFORMATION: Peptide conjugation sequence

<400> SEQUENCE: 12

Gly Phe Leu Gly
1

<210> SEQ ID NO 13
<211> LENGTH: 4
<212> TYPE: PRT
<213> ORGANISM: Artificial Sequence
```

<220> FEATURE:
<223> OTHER INFORMATION: Peptide conjugation sequence

<400> SEQUENCE: 13

Leu Leu Gly Leu
1

<210> SEQ ID NO 14
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 14
cagaagagcc tctgcctgtc cccgggtaaa tga                             33

<210> SEQ ID NO 15
<211> LENGTH: 33
<212> TYPE: DNA
<213> ORGANISM: Artificial Sequence
<220> FEATURE:
<223> OTHER INFORMATION: Mutagenesis oligonucleotide

<400> SEQUENCE: 15
tcatttaccc ggggacaggc agaggctctt ctg                             33

<210> SEQ ID NO 16
<211> LENGTH: 39
<212> TYPE: DNA
<213> ORGANISM: Artificial Sequence
<220> FEATURE:
<223> OTHER INFORMATION: Mutagenesis oligonucleotide

<400> SEQUENCE: 16
ctgtccccgg gtaaatgtgc agcttgagtg cgacggccg                       39

<210> SEQ ID NO 17
<211> LENGTH: 39
<212> TYPE: DNA
<213> ORGANISM: Artificial Sequence
<220> FEATURE:
<223> OTHER INFORMATION: Mutagenesis oligonucleotide

<400> SEQUENCE: 17
cggccgtcgc actcaagctg cacatttacc cggggacag                       39

<210> SEQ ID NO 18
<211> LENGTH: 65
<212> TYPE: DNA
<213> ORGANISM: Artificial Sequence
<220> FEATURE:
<223> OTHER INFORMATION: AACAA anti-sense primer

<400> SEQUENCE: 18
cactctcccc tggatcctca tgcggcgcaa gcggctttac ccggggacag ggagaggctc    60
ttctg                                                              65

<210> SEQ ID NO 19
<211> LENGTH: 62
<212> TYPE: DNA
<213> ORGANISM: Artificial Sequence
<220> FEATURE:
<223> OTHER INFORMATION: CCAA anti-sense primer

```
<400> SEQUENCE: 19
cactctcccc tggatcctca agctgcacag catttacccg gggacaggga gaggctcttc      60
tg                                                                    62

<210> SEQ ID NO 20
<211> LENGTH: 74
<212> TYPE: DNA
<213> ORGANISM: Artificial Sequence
<220> FEATURE:
<223> OTHER INFORMATION: G4SCAA anti-sense primer

<400> SEQUENCE: 20
cactctcccc tggatcctca agctgcgcag gaaccgcccc cacctttacc cggggacagg      60
gagaggctct tctg                                                       74

<210> SEQ ID NO 21
<211> LENGTH: 60
<212> TYPE: DNA
<213> ORGANISM: Artificial Sequence
<220> FEATURE:
<223> OTHER INFORMATION: Forward primer

<400> SEQUENCE: 21
tccaccgcgg tggcggccgc caccatggag tttgggctga gctgggtttt cctcgttgct      60
```